US007138380B2

(12) United States Patent
De La Monte et al.

(10) Patent No.: US 7,138,380 B2
(45) Date of Patent: Nov. 21, 2006

(54) TRANSGENIC ANIMALS AND CELL LINES FOR SCREENING DRUGS EFFECTIVE FOR THE TREATMENT OR PREVENTION OF ALZHEIMER'S DISEASE

(75) Inventors: Suzanne De La Monte, East Greenwich, RI (US); Jack R Wands, Waban, MA (US)

(73) Assignee: The General Hospital Corporation, Boston, MA (US)

( * ) Notice: Subject to any disclaimer, the term of this patent is extended or adjusted under 35 U.S.C. 154(b) by 987 days.

(21) Appl. No.: 09/964,412

(22) Filed: Sep. 28, 2001

(65) Prior Publication Data

US 2002/0129391 A1 Sep. 12, 2002

Related U.S. Application Data

(62) Division of application No. 09/380,203, filed as application No. PCT/US98/03685 on Feb. 26, 1998.

(60) Provisional application No. 60/038,908, filed on Feb. 26, 1997.

(51) Int. Cl.
*A61K 31/70* (2006.01)
*C07H 21/04* (2006.01)
*C07H 21/02* (2006.01)
*C12N 5/00* (2006.01)
*C12Q 1/68* (2006.01)

(52) U.S. Cl. ............................ 514/44; 435/6; 435/375; 435/377; 536/24.1; 536/24.5

(58) Field of Classification Search ................ 435/375, 435/377; 534/24.5, 24.1; 514/44
See application file for complete search history.

(56) References Cited

U.S. PATENT DOCUMENTS

| 4,873,191 A | 10/1989 | Wagner et al. ............ 435/172.3 |
| 5,168,053 A | 12/1992 | Altman et al. ................. 435/91 |
| 5,830,670 A | 11/1998 | de la Monte et al. ......... 435/7.2 |
| 5,948,634 A | 9/1999 | de la Monte et al. ...... 435/69.1 |
| 5,948,888 A | 9/1999 | de la Monte et al. ....... 530/350 |
| 6,071,705 A | 6/2000 | Wands et al. ................. 435/7.1 |
| 6,245,523 B1 | 6/2001 | Altieri ........................ 435/69.1 |

FOREIGN PATENT DOCUMENTS

| EP | 0 263 740 | 4/1988 |
| WO | WO 89/03849 | 5/1989 |
| WO | WO 90/06993 | 6/1990 |
| WO | WO 92/07065 | 4/1992 |
| WO | WO 94/23756 | 10/1994 |
| WO | WO 96/15272 | 5/1996 |
| WO | WO 96/40895 | 12/1996 |

OTHER PUBLICATIONS

Branch A., TIBS vol. 23:45-50, Feb. 1998.*
Jen et al., Stem Cells vol. 18: 307-319, 2000.*
Agrawal S., TIBTECH vol. 14:376-387, Oct. 1996.*
Linder, C.C., "The Influence of Genetic Background on Spontaneous and Genetically Engineered Mouse Models of Complex Diseases," *Lab Animal* 30:34-39, Nature America (May 2001).
Frangiskakis, J.M., et al., "*LIM-kinase1* Hemizygosity Implicated in Impaired Visuospatial Constructive Cognition," *Cell* 86:59-69, Cell Press (Jul. 1996).
Rülicke, T., and Hübscher, U., "Germ line transformation of mammals by pronuclear microinjection," *Exp. Physiol.* 85:589-601, The Physiological Society (Nov. 2000).
Strojek, R.M., and Wagner, T.E., "The Use of Transgenic Animal Techniques for Livestock Improvement," *Genet. Eng.* 10:221-246, Plenum Press (1988).
Houdebine, L.-M., "Production of pharmaceutical proteins from transgenic animals," *J. Biotechnol.* 34:269-287, Elsevier Science B.V. (1994).
Mullins, L.J., and Mullins, J.J., "Transgenesis in the Rat and Larger Mammals," *J. Clin. Invest.* 97:1557-1560, The American Society for Clinical Investigation, Inc. (Apr. 1996).
Bishop, J.O., "Chromosomal insertion of foreign DNA," *Reprod. Nutr. Dev.* 36:607-618, Elsevier/INRA (Nov.-Dec. 1996).
Polejaeva, I.A., and Campbell, K.H.S., "New Advances in Somatic Cell Nuclear Transfer: Application in Transgenesis," *Theriogenology* 53:117-126, Elsevier Science Inc. (Jan. 2000).
Wall, R.J., "Transgenic Livestock: Progress and Prospects for the Future," *Theriogenology* 45:57-68, Elsevier Science Inc. (Jan. 1996).
Sigmund, C.D. "Viewpoint: Are Studies in Genetically Altered Mice Out of Control?" *Arterioscler. Thromb. Vasc. Biol.* 20:1425-1429, Lippincott Williams & Wilkins (Jun. 2000).
Chiu, T.-L., and Goldstein, R.A., "Optimizing energy potentials for success in protein tertiary structure prediction," *Fold. Des.* 3:223-228, Current Biology Ltd. (May 1998).

(Continued)

*Primary Examiner*—Sean McGarry
(74) *Attorney, Agent, or Firm*—Sterne, Kessler, Goldstein & Fox P.L.L.C.

(57) ABSTRACT

Disclosed are transgenic animals and transfected cell lines expressing a protein associated with Alzheimer's Disease, neuroectodermal tumors, malignant astrocytomas, and glioblastomas. Also disclosed is the use of such transgenic animals and transfected cell lines to screen potential drug candidates for treating or preventing Alzheimer's disease, neuroectodermal tumors, malignant astrocytomas, and glioblastomas. The invention also relates to new antisense oligonucleotides, ribozymes, triplex forming DNA and external guide sequences that can be used to treat or prevent Alzheimer's disease, neuroectodermnal tumors, malignant astrocytomas, and glioblastomas.

7 Claims, 13 Drawing Sheets

OTHER PUBLICATIONS

Ngo, J.T., et al., "Computational Complexity, Protein Structure Prediction, and the Levinthal Paradox," in *The Protein Folding Problem and Tertiary Structure Prediction*, Merz, K. Jr., and Le Grand, S., eds., Birkhauser, Boston, MA, pp. 491-495 (1994).

Yamada, K., and Nabeshima, T., "Animal models of Alzheimer's disease and evaluation of anti-dementia drugs," *Pharmacol. Ther.* 88:93-113, Elsevier Science Inc. (Nov. 2000).

Anderson, W.F., "Human gene therapy," *Nature* 392:25-30, Macmillan Journals Ltd. (Apr. 1998).

Bloch, D.B., et al., "Identification and Characterization of a Leukocyte-specific Component of the Nuclear Body," *J. Biol. Chem.* 271:29198-29204, The American Society for Biochemistry and Molecular Biology, Inc. (Nov. 1996).

Brinster, R.L., et al., "Factors affecting the efficiency of introducing foreign DNA into mice by microinjecting eggs," *Proc. Natl. Acad. Sci. USA* 82:4438-4442, National Academy of Sciences (1985).

Chiu, T.-L. and Goldstein, R.A., "Optimizing energy potentials for success in protein tertiary structure prediction," *Folding and Design* 3:223-228, Current Biology Ltd. (May 1998).

de la Monte, S.M., et al., "Enhanced Expression of an Exocrine Pancreatic Protein in Alzheimer's Disease and the Developing Human Brain," *J. Clin. Invest.* 86:1004-1013, The American Society for Clinical Investigation, Inc. (1990).

de la Monte, S.M., et al., "Regional and Maturation-associated Expression of Endothelin 2 in Rat Gastrointestinal Tract," *J. Histochem. Cytochem.* 43:203-209, The Histochemical Society, Inc. (1995).

de la Monte, S.M., et al., "Aberrant GAP-43 Gene Expression in Alzheimer's Disease," *Am. J. Pathol.* 147:934-946, American Society for Investigative Pathology (1995).

de la Monte, S.M., and Bloch, K.D., "Aberrant Expression of the Constitutive Endothelial Nitric Oxide Synthase Gene in Alzheimer Disease," *Mol. Chem. Neuropathol.* 30:139-159, Humana Press, Inc. (Jan./Feb. 1997).

Games, D., et al., "Alzheimer-type neuropathology in transgenic mice overexpressing V717F β-amyloid precursor protein," *Nature* 373:523-527, Macmillan Journals Ltd. (1995).

Gossler, A., et al., "Transgenesis by means of blastocyst-derived embryonic stem cell lines," *Proc. Natl. Acad. Sci. USA* 83:9065-9069, National Academy of Science (1986).

Gross, J., et al., "Isolation Characterization, and Distribution of an Unusual Pancreatic Human Secretory Protein," *J. Clin. Invest.* 76:2115-2126, The American Society for Clinical Investigation, Inc. (1985).

The Huntington's Disease Collaborative Research Group, "A Novel Gene Containing a Trinucleotide Repeat That Is Expanded and Unstable on Huntington's Disease Chromosomes," *Cell* 72:971-983, Cell Press (1993).

Kosaka, K., "Dementia and Neuropathology in Lewy Body Disease," *Adv. Neurol.* 60:456-463, Raven Press. Ltd. (1993).

Lannfelt, L., et al., "Alzheimer's disease: molecular genetics and transgenic animal models," *Behav. Brain Res.* 57:207-213, Elsevier Science B.V. (1993).

Marx, J., "Major Setback for Alzheimer's Models," *Science* 255:1200-1202, American Association for the Advancement of Science (1992).

Ozturk, M., et al., "Elevated levels of an exocrine pancreatic secretory protein in Alzheimer disease brain," *Proc. Natl. Acad. Sci. USA* 86:419-423, National Academy of Sciences (1989).

Pursel, V.G., et al., "Genetic Engineering of Livestock," *Science* 244:1281-1288, American Association for the Advancement of Science (1989).

Quon, D., et al., "Formation of β-amyloid protein deposits in brains of transgenic mice," *Nature* 352:239-241, Macmillan Journals Ltd. (1991).

Salter, D.W., et al., "Transgenic Chickens: Insertion of Retroviral Genes into the Chicken Germ Line," *Virology* 157:236-240, Academic Press, Inc. (1987).

Verma, I.M. and Somia, N., "Gene Therapy- promises, problems and prospects," *Nature* 389:239-242, Macmillan Journals Ltd. (Sep. 1997).

Dialog File 351, Accession No. 88-100135/198815, Derwent WPI English language abstract for EP 0 263 740 (Document AL1).

International Search Report for International Application No. PCT/US98/03685, mailed Jul. 9, 1998.

Pending Non-Provisional U.S. Appl. No. 09/380,203, de la Monte et al., filed Apr. 25, 2000 and U.S. Appl. No. 09/964,678, 09/964,666 and 09/964,667, de la Monte et al., filed Sep. 28, 2001.

Claims Currently Pending from U.S. Appl. No. 09/380,203, de la Monte et al., filed Apr. 25, 2000.

Claims Currently Pending from U.S. Appl. No. 09/964,678, de la Monte et al., filed Sep. 28, 2001.

Claims Currently Pending from U.S. Appl. No. 09/964,666, de la Monte et al., filed Sep. 28, 2001.

Claims Currently Pending from U.S. Appl. No. 09/964,667, de la Monte et al., filed Sep. 28, 2001.

* cited by examiner

```
   1 tttttttttttgag ATG GAG TTT TCG CTC TTG TTG CCC AGG CTG GAG TGC AAT GGC GCA ATC    62
   1                 M   E   F   S   L   L   L   P   R   L   E   C   N   G   A   I    16

63 TCA GCT CAC CGC AAC CTC CGC CTC CCG GGT TCA AGC GAT TCT CCT GCC TCA GCC TCC CCA  122
  17  S   A   H   R   N   L   R   L   P   G   S   S   D   S   P   A   S   A   S   P   36

123 GTA GCT GGG ATT ACA GGC ATG TGC ACC CAC GCT CGG CTA ATT TTG TAT TTT TTT TTA GTA  182
  37  V   A   G   I   T   G   M   C   T   H   A   R   L   I   L   Y   F   F   L   V   56

183 GAG ATG GAG TTT CTC CAT GTT GGT CAG GCT GGT CTC GAA CTC CCG ACC TCA GAT GAT CCC  242
  57  E   M   E   F   L   H   V   G   Q   A   G   L   E   L   P   T   S   D   D   P   76

243 TCC GTC TCG GCC TCC CAA AGT GCT AGA TAC AGG ACT GGC CAC CAT GCC GGC CTC TGC CTG  302
  77  S   V   S   A   S   Q   S   A   R   Y   R   T   G   H   H   A   R   L   C   L   96

303 GCT AAT TTT TGT GGT AGA AAC AGG GTT TCA CTG ATG TGC CCA AGC TGG TCT CCT GAG CTC  362
  97  A   N   F   C   G   R   N   R   V   S   L   M   C   P   S   W   S   P   E   L  116

363 AAG CAG TCC ACC TGC CTC AGC CTC CCA AAG TGC TGG GAT TAC AGG CGT GCA GCC GTG CCT  422
 117  K   Q   S   T   C   L   S   L   P   K   C   W   D   Y   R   R   A   A   V   P  136

423 GGC CTT TTT ATT TTA TTT TTT TTA AGA CAC AGG TGT CCG ACT CTG TCG CAG ACG ATG AGG  482
 137  G   L   F   I   L   F   F   L   R   H   R   C   P   T   L   T   Q   D   E   V  156

483 CAG TGG TGT GAT CAG AGC AGC TCA CAG CCG TCG ACA CCT GAG ATC AAG CAT CCT GCT TGG  542
 157  Q   W   C   D   H   S   S   L   Q   P   S   T   P   E   I   K   H   P   A   W  176

543 TCA GCC TCG CAG GTA GCT GGT ACC AAG GAC ATG CAC TAC TGG CTA ATT TTT ATT  602
 177  S   A   S   Q   V   A   G   T   K   D   M   H   Y   W   L   I   F   I  196

603 TTT ATT TTT AAT TTT CTG AGA CAG AGT CTC GAC TCT GTC ACC CAG GCT GGA GTG CAG TGG  662
 197  F   I   F   N   F   L   R   Q   S   L   N   S   V   T   Q   A   G   V   Q   W  216

663 CGG AAT CTT GGG TCA CTG CAA CCT CTG CCT CCC GGG GGC TTC AAG CTA TTC TCC TGG CCT  722
 217  R   N   L   G   S   L   Q   P   L   P   P   G   F   K   L   F   S   C   P   S  236

723 CTC CTG AGT AGG AGG GAT TAC AGG TGC CGA CCA CCG CTA GCT AAT TTT GTA TTT TTA  782
 237  L   L   S   W   D   Y   R   R   P   P   R   L   A   N   F   V   F   L  256

783 GTA GAG ATG GGG TTC ACC ATG TTC GGG AGG TTG GTG TCG ATC TCC TGG CCT CAG CCG  842
 257  V   E   M   G   F   T   M   F   A   R   L   I   L   I   S   G   P   C   D   L  276

843 CCT GCC TCG GCC TCC CAA AGT GCT GGG ATT ACA GGC GTG AGC CAC CAC GCC CGG CTT ATT  902
 277  P   A   S   A   S   Q   S   A   G   I   T   G   V   S   H   H   A   R   L   I  296

903 TTT AAT TTT TGT TTG TTT GAA ATG GAA TCT CAC TCT GTT ACC CAG GCT GGA GTG CAA TGG  962
 297  F   N   F   C   L   F   E   M   E   S   H   S   V   T   Q   A   G   V   Q   W  316

963 CCA AAT CTC GGC TCA CTG CAA CCT CTG CCT CCC GGG CTC AAG CGA TTC TCC TGT CTC AGC 1022
 317  P   N   L   G   S   L   Q   P   L   P   P   G   L   K   R   F   S   C   L   S  336

1023 CTC CCA AGC AGC TGG GAT TAC GGG CAC CTG CCA CCA CAC CCC GCT AAT TTT TGT ATT TTC 1082
 337  L   P   S   S   W   D   Y   G   H   L   P   P   H   P   A   N   F   C   I   F  356

1083 ATT AGA GGC GGG GTT TCA CCA TAT TTG TCA GGC TGG TCT CAA ACT CCT GAC CTC AGG tgac 1143
 357  I   R   G   G   V   S   P   Y   L   S   G   W   S   Q   T   P   D   L   R       375

1144 ccacctgcctcagccttccaaagtgctgggattacaggcgtgagccacctcacccagccggctaatttagataaaaaat 1223

1224 atgtagcaatggggggtcttgctatgttgcccaggctggtctcaaacttctggcttcatgcaatccttccaaatgagcca 1303

1304 caacacccagccagtcacatttttttaaacagttacatctttattttagtatactagaaagtaatacaataaacatgtcaa 1383

1384 acctgcaaattcagtagtaacagagttctttttataacttttaaacaaagctttagagca                     1442
```

FIG. 1

FIGS. 2A-2F
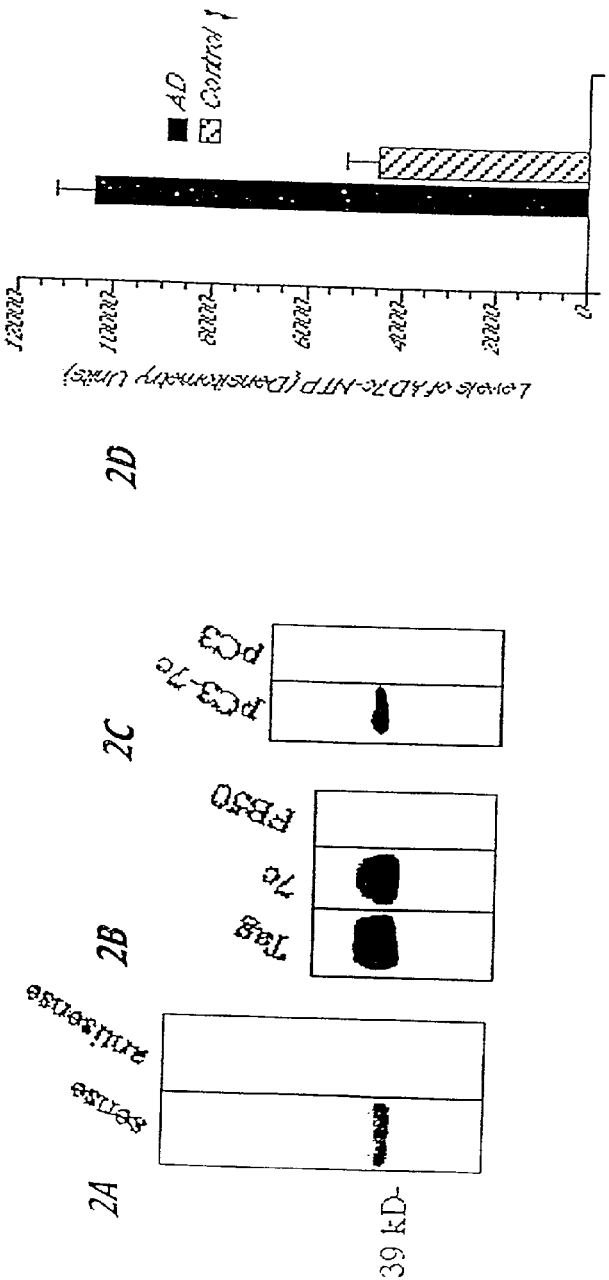
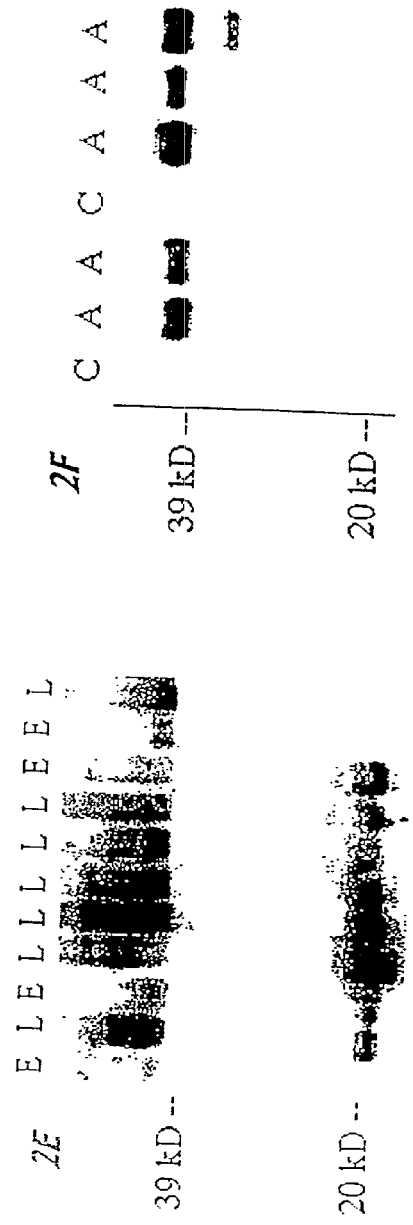

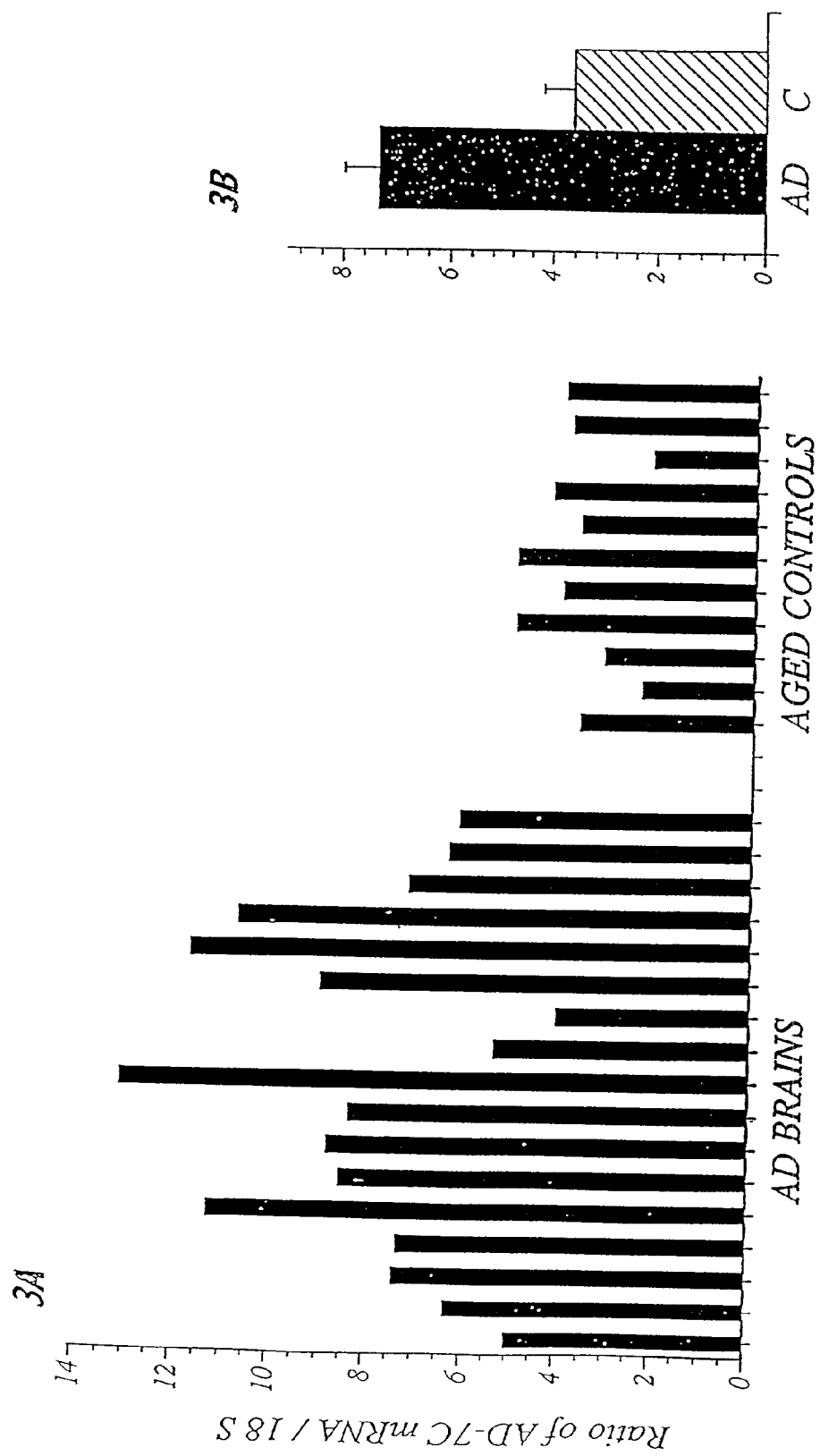

TRANSGENIC ANIMALS AND CELL LINES FOR SCREENING DRUGS EFFECTIVE FOR THE TREATMENT OR PREVENTION OF ALZHEIMER'S DISEASE

STATEMENT AS TO RIGHTS TO INVENTIONS MADE UNDER FEDERALLY-SPONSORED RESEARCH AND DEVELOPMENT

This invention was made with U.S. Government support under grant nos. CA-35711, AA-00026 and AA-002169, awarded by the National Institutes of Health. The U.S. Government has certain rights in this invention.

BACKGROUND OF THE INVENTION

1. Field of the Invention

The present invention is in the field of genetic engineering and molecular biology. In particular, the invention is directed to transgenic animals and transfected cell lines expressing a protein associated with Alzheimer's Disease, neuroectodermal tumors, malignant astrocytomas, and glioblastomas. This invention is also directed to the use of such transgenic animals and transfected cell lines to screen potential drug candidates for treating or preventing Alzheimer's disease. The invention also relates to new antisense oligonucleotides, ribozymes, triplex forming DNA and external guide sequences that can be used to treat or prevent Alzheimer's disease.

2. Related Art

Alzheimer's disease (AD) (Khachaturian, Z. S., "Diagnosis of Alzheimer's Disease," *Arch. Neurol.* 421:1097–1105 (1985)) is the most prevalent neurodegenerative disease and the most common cause of dementia in the Western hemisphere. AD neurodegeneration is characterized by prominent atrophy of corticolimbic structures with neuronal loss, neurofibrillary tangle formation, aberrant proliferation of neurites, senile plaques, and βA4-amyloid deposition in the brain (Khachaturian, Z. S.). Approximately 90 percent of AD occurs sporadically. The cause is unknown, but the most important overall risk factor is aging (Takman, A., "Epidemiology of Alzheimer's Disease. Issues of Etiology and Validity," *Acta Neurol. Scand. Suppl.* 145: 1–70(1993)). The apolipoprotein ∈4 genotype (Corder, E. H. et al., "Gene Does of Apolipoprotein E Type 4 Allele and the Risk of Alzheimer's Disease in Late Onset Families, *Science* 261:921–923 (1993)) and a family history of Trisomy 21 Down syndrome (Lai, F. and Williams, R. S., "A Prospective Study of Alzheimer Disease in Down Syndrome," *Arch. Neurol.* 46:849–853 (1989) increase risk or accelerate the course of sporadic AD. Familial forms of AD, which account for 5 to 10 percent of the cases, have been linked to mutations in the amyloid precursor protein (APP) gene (Kennedy, A. M. et al., "Familial Alzheimer's Disease. A Pedigree With a Mis-Sense Mutation in the Amyloid Precursor Protein Gene (Amyloid Precursor Protein 717 Valine→Glycine," *Brain* 309–324 (1993); Peacock, M. L. et al., "Novel Amyloid Precursor Protein Gene Mutation (Codon 665Asp) in a Patient with Late-Onset Alzheimer's Disease," *Ann. Neurol.* 35:432–438 (1994); Tanzi, R. E. et al., "Assessment of Amyloid Beta-Protein Precursor Gene Mutations in a Large Set of Familial and Sporadic Alzheimer's Disease Cases," *Am. J. Hum. Genet.* 51:273–282 (1992)) located on Chromosome 21 (Robakis, N. K. et al., Chromosome 21q21 Sublocalization of Gene Encoding Beta-Amyloid Peptide in Cerebral Vessels and Neuritic (Senile) Plaques of People with Alzheimer Disease and Down Syndrome," *Lancet* 1:384–385 (1987)), or presenilin genes located on Chromosomes 1 and 14 (Levy-Lahad, E. et al., "Candidate Gene for the Chromosome 1 Familial Alzheimer's Disease Locus," *Science* 18:973–977 (1995); Sorbi, S. et al., "Missense Mutation of S 182 Gene in Italian Families With Early Onset Alzheimer's Disease," *Lancet* 346:439–440 (1995); Sherrington, R. et al., "Cloning of a Gene Bearing Missense Mutations in Early-Onset Familial Alzheimer's Disease, *Nature* 375:754–760 (1995); Rogaev, E. I. et al., "Familial Alzheimer's Disease in Kindreds With Missense Mutations in a Gene on Chromosome 1 Related to the Alzheimer's Disease Type 3 Gene," *Nature* 376:775–778 (1995); Barinaga, M. et al., "Candidate Gene for the Chromosome 1 Familial Alzheimer's Disease Locus," *Science* 269:973–977 (1995)). Over-expression and abnormal cleavage of APP may promote AD neurodegeneration since all individuals with Trisomy 21 Down syndrome who survive beyond the fourth decade develop AD with extensive central nervous system (CNS) accumulations of βA4-amyloid (Lai, F. and Williams, R. S., "A Prospective Study of Alzheimer Disease in Down Syndrome," *Arch. Neurol.* 46:849–853 (1989)), and experimentally, βA4-amyloid is neurotoxic and apoptogenic (LaPerla, F. M. et al., "The Alzheimer's A Beta Peptide Induces Neurodegeneration and Apoptotic Cell Death in Transgenic Mice," *Nat. Genet.* 9:21–30 (1995). In addition, missense mutations in persenilin 1, as occurs in nature, cause vasculopathy and massive accumulations of peptides in the brain (Lemere, C. A. et al., "The E280A Presenilin 1Alzheimer Mutation Produces Increased Aβ42 Deposition and Severe Cerebellar Pathology," *Nature Med.* 2:1146–1150 (1996); Mann, D. M. et al., "Amyloid Beta Protein (Abeta) Deposition in Chromosome 14-Linked Alzheimer's Disease: Predominance of Abeta42(43)," *Ann Neurol.* 40:149–156 (1996)).

Central nervous system biochemical and molecular abnormalities identified in AD include: 1) increased phosphorylation of tau and other cytoskeletal proteins in neurons (Grundke-Iqbal, I. et al., "Abnormal Phosphorylation of the Microtubule-Associated Protein π (tau) in Alzheimer Cytoskeletal Pathology," *Proc. Natl. Acad. Sci. U.S.A.* 83:4913–4917 (1986)); 2) aberrant expression of genes modulated with neuritic sprouting such as the growth associated protein, GAP-43 (de la Monte, S. M. et al., "Aberrant GAP-43 Gene Expression in Alzheimer's Disease," *Am. J. Pathol.* 147:934–946 (1995)), constitutive endothelial nitric oxide synthase (de la Monte, S. M. and Bloch, K. D. "Aberrant Expression of the Constitutive Endothelial Nitric Oxide Synthase Gene in Alzheimer's Disease," *Molecular and Chemical Neuropathy* 29: (in press)) transforming growth factor β (Peress, N. S. and Perillo, E., "Differential Expression of TGF-beta 1, 2, and 3 Isotypes in Alzheimer's Disease: a Comparative Immunohistochemical Study With Cerebral Infarction, Aged Human and Mouse Control Brains," *J. Neuropathol. Exp. Neurol.* 54: 802–811 (1995)), and metallothionine-3 (Aschner, M. "The Functional Significance of Brain Metallothioneins," *Faseb. J.* 10:1129–1136 (1996)); 3) increased expression of genes associated with glial cell activation, such as glial fibrillary acidic protein (Goodison, K. L. et al., "Neuronal and Glial Gene Expression in Neocortex of Down's Syndrome," *J. Neuropathol. Exp. Nerol.* 52:192–198 (1993)) and alpha-1 antichymotrypsin (Pastemack, J. M. et al., "Astrocytes in Akizheimer's Disease Gray Matter Express Alpha 1-Antichymotrypsin mRNA," *Am. J. Path.* 135:827–834 (1989); and 4) altered expression of genes that protect neurons from either cytotoxic or programmed cell death, including sulfated glycoprotein-2 (May, P. C. et al., "Dynamics of Gene Expression for a Hippocampal Glycoprotein Elevated in Alzheimer's Disease and in Response to Experimental Lesions in Rat," *Neuron* 5:831–839 (1990), cathepsin D (Cataldo, A. M. et al., "Gene Expression and Cellular Content of Cathepsin D in Alzheimer's Disease Brain: Evidence for Early Up-Regulation of theEndosomal-Lysosomal System," *Neuron* 14:671–680 (1995)), superoxide dismutase 1 (Somerville, M. J. et al., "Localization and Quantitation of 68 kDA Neurofilament and Superoxide Dismutase-1 mRNA in Alzheimer Brains, *Brain Res. Mol. Brain Res.* 9:1–8 (1991), mitochondrial cytochrome oxidase (Chandrasekaran, K. et al., "Impairment in Mitochondrial Cytochrome Oxidase Gene Expression In Alzheimer Disease," *Brain Res. Mol. Brain. Res.* 24:336–340 (1994)), C1q component of complement (Fischer, B. et al., "Complement C1q and C3 mRNA Expression in the Frontal Cortex of Alzheimer's Patients," *J. Mol. Med.* 73:465–471 (1995)), Calbindin D28k (Yamagishi, M. et al., "Ontogenetic Expression of Spot 35 Protein (Calbindin-D28k) in Human Olfactory Receptor Neurons and its Decrease in Alzheimer's Disease Patients," *Ann. Ontol. Rhinol. Laryngol.* 105:132–139 (1996), and bcl-2 (O'Barr, S. et al., "Expression of the Protooncogene bcl-2 in Alzheimer's Disease Brain," *Neurobiol. Aging* 17:131–136 (1996).

In previous studies, we demonstrated increased immunoreactivity in AD brains using a polyclonal antisera prepared against a pancreatic protein (Ozturk, M. et al., "Elevated Levels of an Exocrine Pancreatic Secretory Protein in Alzheimer's Disease Brain," *Proc. Natl. Acad. Sci. U.S.A.* 86:419–423 (1989); de la Monte, S. M. et al., "Enhanced Expression of an Exocrine Pancreatic Protein in Alzheimer's Disease and the Developing Human Brain," *J. Clin. Invest.* 86:1004–1013 (1990); WO90/06993). Using such polyclonal antibodies, we isolated the AD7c-NTP cDNA from an AD brain expression library (WO94/23756). In WO94/23756, this clone is also referred to as AD10-7, which was deposited in DH1 cells at the ATCC under accession no. 69262. The nucleotide sequence of this cDNA is shown in FIG. 16R of WO94/23756. However, this sequence comprises numerous errors. See also WO96/15272 (Seq. ID No. 120, pages 168–170), which also comprises numerous errors. As a result, the predicted amino acid sequence (Seq. ID No. 121; WO96/15272) is also wrong.

SUMMARY OF THE INVENTION

The present invention is related to transgenic animals and cell lines which over express the AD7c-NTP and use thereof to screen candidate drugs for use in the treatment or prevention of Alzheimer's disease, neuroectodermal tumors, malignant astrocytomas and glioblastomas.

In particular, the invention relates to a DNA construct, wherein said DNA construct comprises a DNA molecule having Seq. ID No. 1 or a DNA sequence at least 40% homologous thereto, or a fragment thereof. Preferably, the DNA molecule is under control of a heterologous, neuro-specific promoter.

The invention also relates to cell lines containing the DNA construct of the invention.

The invention also relates to transgenic non-human animals which comprise the DNA construct of the invention. Preferably, the transgenic animals over-express AD7c-NTP.

The invention also relates to an in vitro method for screening candidate drugs that are potentially useful for the treatment or prevention of Alzheimer's disease, neuroectodermal tumors, malignant astrocytomas, and glioblastomas, which comprises (a) contacting a candidate drug with a host transfected with a DNA construct, wherein the DNA construct comprises a DNA molecule of Seq. ID No. 1 or a DNA molecule at least 40% homologous thereto, or a fragment thereof, and wherein said host over expresses the protein coded for by said DNA molecule, and (b) detecting at least one of the following:
   (i) the suppression or prevention of expression of the protein;
   (ii) the increased degradation of the protein; or
   (iii) the reduction of frequency of at least one of neuritic sprouting, nerve cell death, degenerating neurons, neurofibrillary tangles, or irregular swollen neurites and axons in the host;

due to the drug candidate compared to a control host that has not received the candidate drug.

In a preferred embodiment, the host is a transgenic animal. In another preferred embodiment, the host is a cell in vitro.

The invention is also directed to antisense oligonucleotides which are complementary to an NTP nucleic acid sequence and which is nonhomologous to PTP nucleic acid sequences and that correspond to regions that were incorrectly sequenced in the past, as well as pharmaceutical compositions comprising such oligonucleotides and a pharmaceutically acceptable carrier.

The invention is also directed to ribozymes comprising a target sequence which is complementary to an NTP sequence and nonhomologous to PTP nucleic acid sequences and that correspond to regions that were incorrectly sequenced in the past, as well as pharmaceutical compositions comprising such ribozymes and a pharmaceutically acceptable carrier.

The invention is also directed to oligodeoxynucleotides that form triple stranded regions with the AD7c-NTP gene, which are nonhomologous to PTP nucleic acid sequences, and that correspond to regions that were incorrectly sequenced in the past, as well as pharmaceutical compositions comprising such oligodeoxynucleotides and a pharmaceutically acceptable carrier.

The invention is also directed to a method of achieving pharmaceutical delivery of the antisense oligonucleotides, ribozymes and triple helix oligonucleotides to the brain through acceptable carriers or expression vectors.

The invention is also directed to the therapeutic use of the antisense oligonucleotides, ribozymes and triple helix oligonucleotides to modify or improve dementias of the Alzheimer's type of neuronal degeneration; as well as to treat or prevent neuroectodermal tumors, malignant astrocytomas, and glioblastomas.

BRIEF DESCRIPTION OF THE DRAWINGS

FIGS. 1A–1C depict the nucleotide and translated amino acid sequence (Seq ID Nos. 1 and 2) of the AD7c-NTP cDNA. The shaded region corresponds to the nucleic acid sequences detected in 6 AD brains by RT-PCR analysis of mRNA. The cDNA exhibits significant homology with Alu gene, and to an unknown gene in the Huntington region, Chromosome 4q16.3 (underlined). The open reading frame begins with the first methionine codon. The translated amino acid sequence encodes a 41.3 kD protein with a hydrophobic leader sequence (italics) followed by a myristoylation motif (bold, italics) and potential Al cleavage site. That same region (italics, underlined) exhibits significant homology with the insulin/IUF- 1 chimeric receptor. There are 17 potential glycogen synthase kinase-3, protein kinase C, or cAMP or Ca-dependent kinase II phosphorylation motifs and one transforming growth factor (tgf) motif (double underlined). The embolded amino acid sequences exhibit significant homology with the A4 alternatively spliced mutant form of NF2, β subunit of integrin, and human decay accelerating factor 2 precursor. The boxed amino acid sequences exhibit significant homology with human integral membrane protein and myelin oligoglycoprotein-16.

FIGS. 2A–2F depict AD7c-NTP expression in vitro and in vivo. (2A): Recombinant protein detected by in vitro translation using sense strand cRNA transcripts. (2B): Western blot analysis of purified recombinant protein demonstrating specific immunoreactivity with the Tag and N314 AD7c-NTP monoclonal antibodies, but not with non-relevant FB50 monoclonal antibody. (2C): Western blot analysis of BOSC cells stably transfected with pcDNA3-AD7c-NTP or pcDNA3 (empty vector). The blots were probed with the N314 AD7c-NTP antibody. (2D): Significantly increased levels of the 41–45 kD AD7c-NTP protein in AD frontal lobe relative to age-matched control frontal lobe tissue. Similar results were obtained for temporal lobe tissue. (2E): Higher levels of the 41–45 kD and 19–21 kD AD7c-NTP proteins in late, end-stage (L) AD compared with early, less symptomatic (B) AD. All tissue samples were taken from the frontal lobe. Note the clusters of 3 or 4 bands between ~41 and ~45 kD, probably corresponding to different degrees of phosphorylation. (2F): Western blot analysis of postmortem ventricular fluid demonstrating higher levels of the ~41 kD AD7c-NTP molecules in AD compared with aged control samples using the N3I4 antibody. The ~28–30 kD band may represent a degradation product. Also note detection of the ~19–21 kD N3I4-imunoreactive molecules in AD.

FIGS. 3A–3F depict AD7c-NTP mRNA expression in AD and aged control brains. Northern blot analysis of AD and aged control frontal lobe RNA detected ~1.4 kB transcripts corresponding to the size of the AD&c-NTP cDNA. In addition, ~0.9 kB transcripts corresponding to a different cDNA were detected in all brains, but not in other tissues. Densitometric analysis of the autoradiograms revealed variable levels of AD7c-NTP mRNA expression in the AD group (3A), but significantly higher mean levels of the 1.4 kB AD7c-NTP transcript in the AD (N=17) relative to the aged control (N=11) group (P<0.01). (FIGS. 3C and 3D): Brightfield photomicrographs of in situ hybridization results using antisense (3C) or sense (3D; negative control) digoxigenin-labeled cRNA probes. Arrows indicate examples of neurons and dark grains represent positive hybridization signals. (FIGS. 3E and 3F): Darkfield photomicrographs of in situ hybridization results demonstrating more intense labeling (white grains) in AD (3E) relative to aged control (3F) cortical neurons (arrows) in the frontal lobe. Probe labeling was detected with antidigoxigenin and alkaline phosphatase substrates (see below). The white signals aggregated over neurons (pyramidal shaped) represent positive results, and black areas indicate absent probe binding.

Figure 3C:
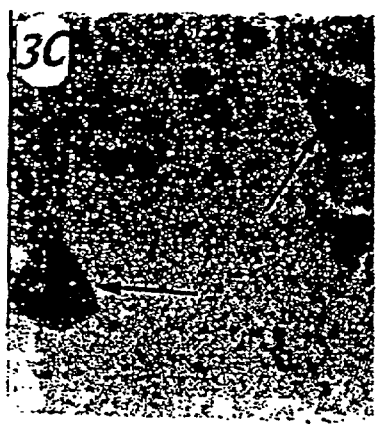
Figure 3D:
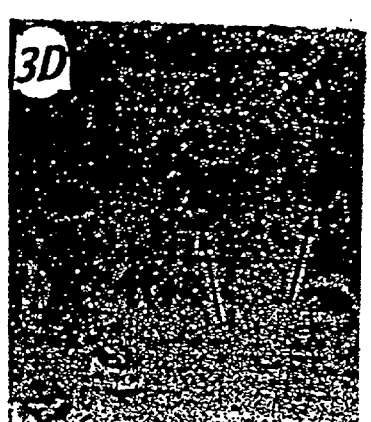
Figure 3E:
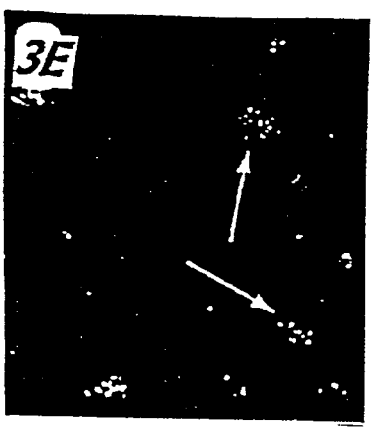
Figure 3F:
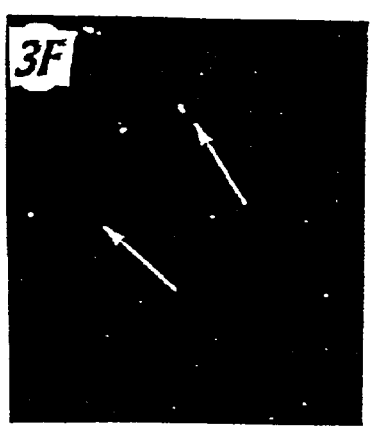
Figures 4A, 4B, 4C, 4D, 4E, 4F, 4G, 4H:
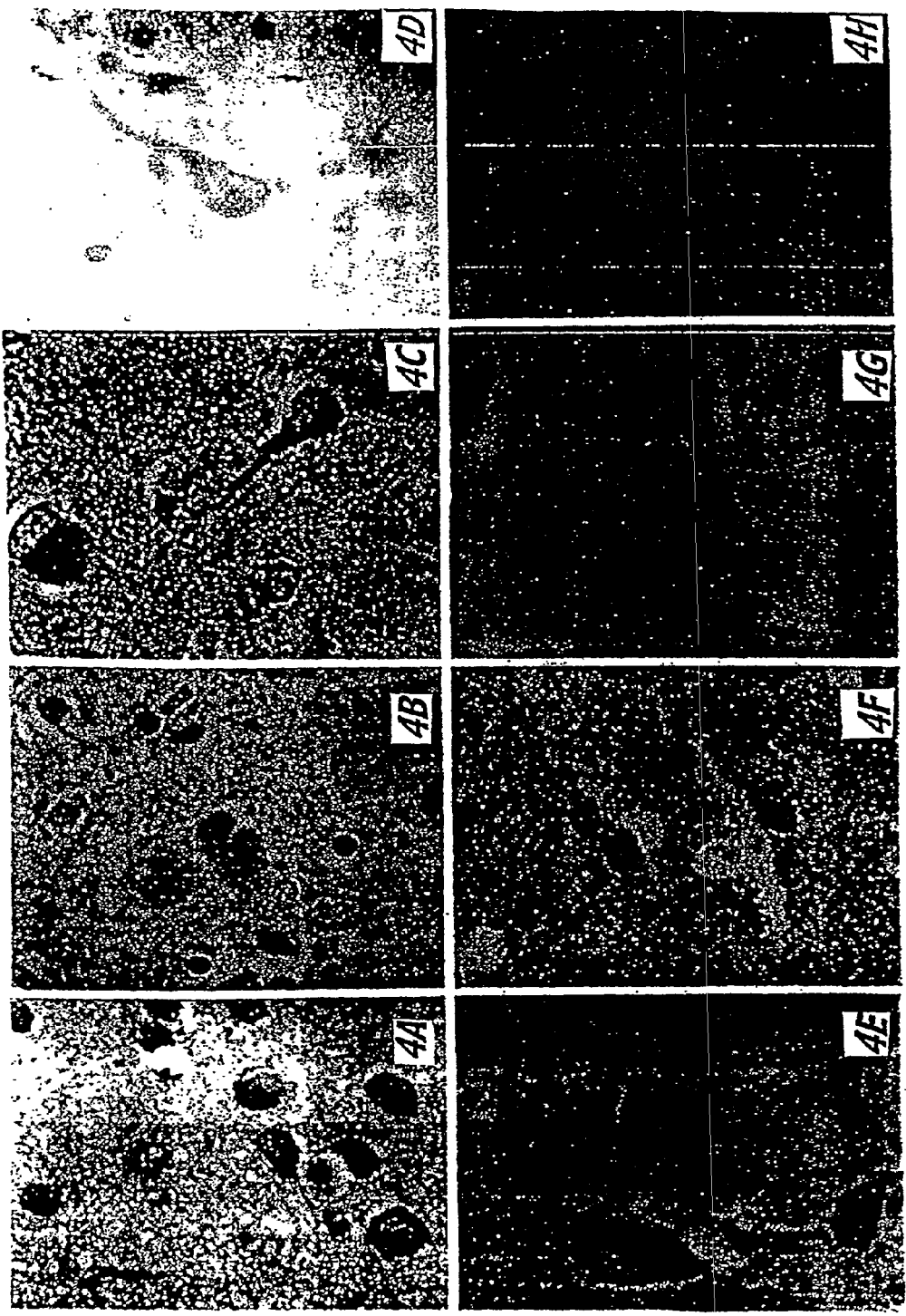

FIGS. 4A–4H depict increased AD7c-NTP immunoreactivity in AD (4A) relative to aged control (4B) cortical neurons by immunohistochemical staining with the N2T8 (4A and 4B). N2J1 immunoreactivity in AD brains (FIGS. 4C, 4E–4H) demonstrating high-level AD7c-NTP expression or accumulation in the perikarya of cytologically intact (4C) as well as degenerating (4E) neurons. In addition, the N2J1 antibody was immunoreactive with abnormal dystrophic cell processes occurring in aggregates (sprouts) (4F), dispersed in the white matter (4G), and corresponding to irregular beaded axons (4H). FIG. 4D depicts AD cerebral cortex immunostained with non-relevant antibody. The sections in FIGS. 4A and 4B were counter stained with hematoxylin to provide a contrasting background.

Figure 5A:
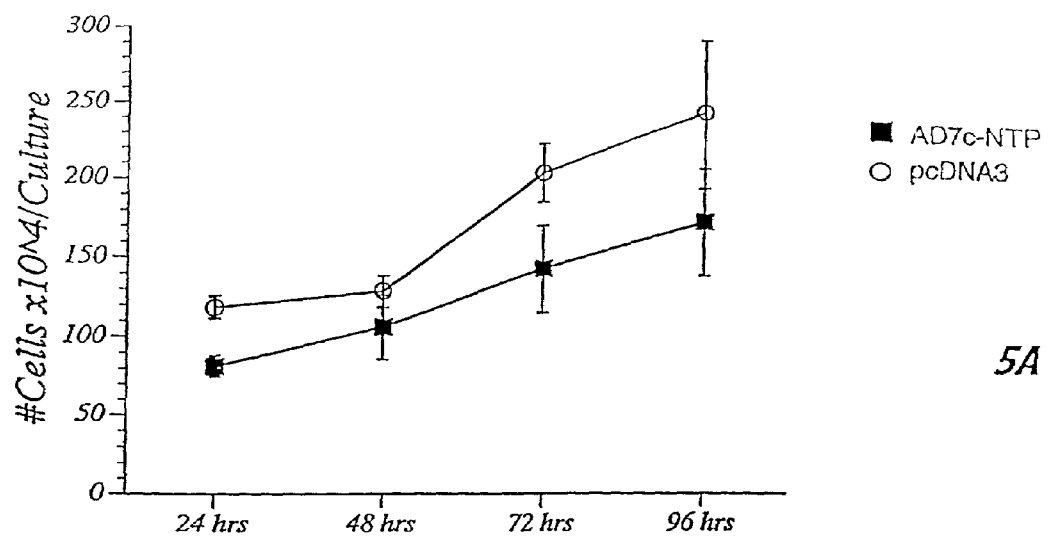
Figure 5B:
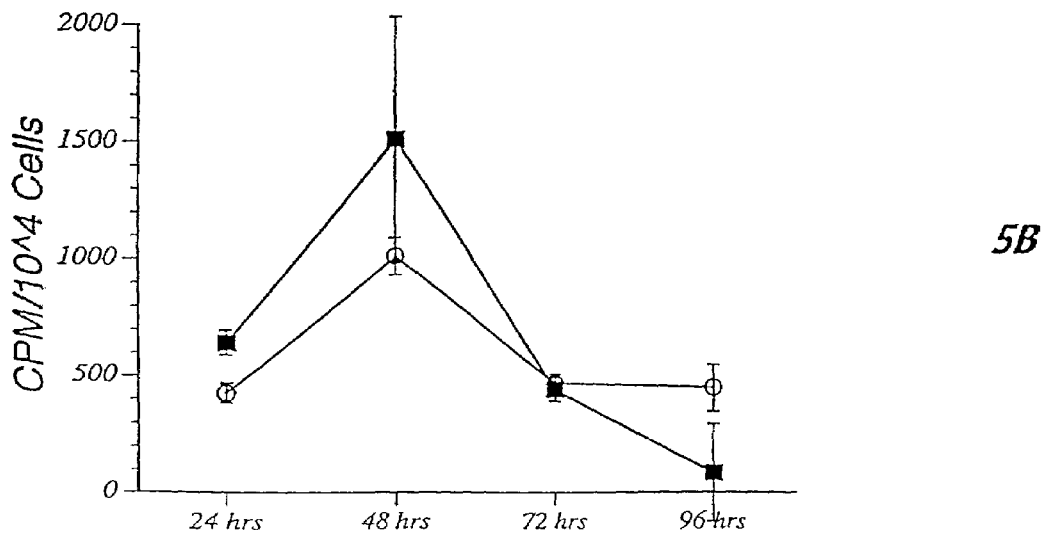

FIGS. 5A and 5B depict graphs showing increased cell death in pcDNA3-AD7c-NTP transfected SH-Sy5y cells. Synchronized cells were fed with medium containing 10% fetal calf serum, and DNA synthesis was assessed by $^3$H-thymidine incorporation into DNA (5A). The density of viable cells was determined at each time point (5A). Despite higher levels of DNA synthesis (5B), cell density was significantly reduced in 4 replicate AD7c-NTP-transfected cultures compared with control (pcDNA3-transfected) cells. AD7c-NTP-transfected cells also exhibited increased nuclear p53 immunoreactivity and increased nuclear DNA fragmentation by the in situ assay for nicked DNA (TUNEL), suggesting that over-expression of AD7c-NTP in neuronal cells causes apoptosis.

Figures 6A, 6B, 6C, 6D, 6E, 6F, 6G:
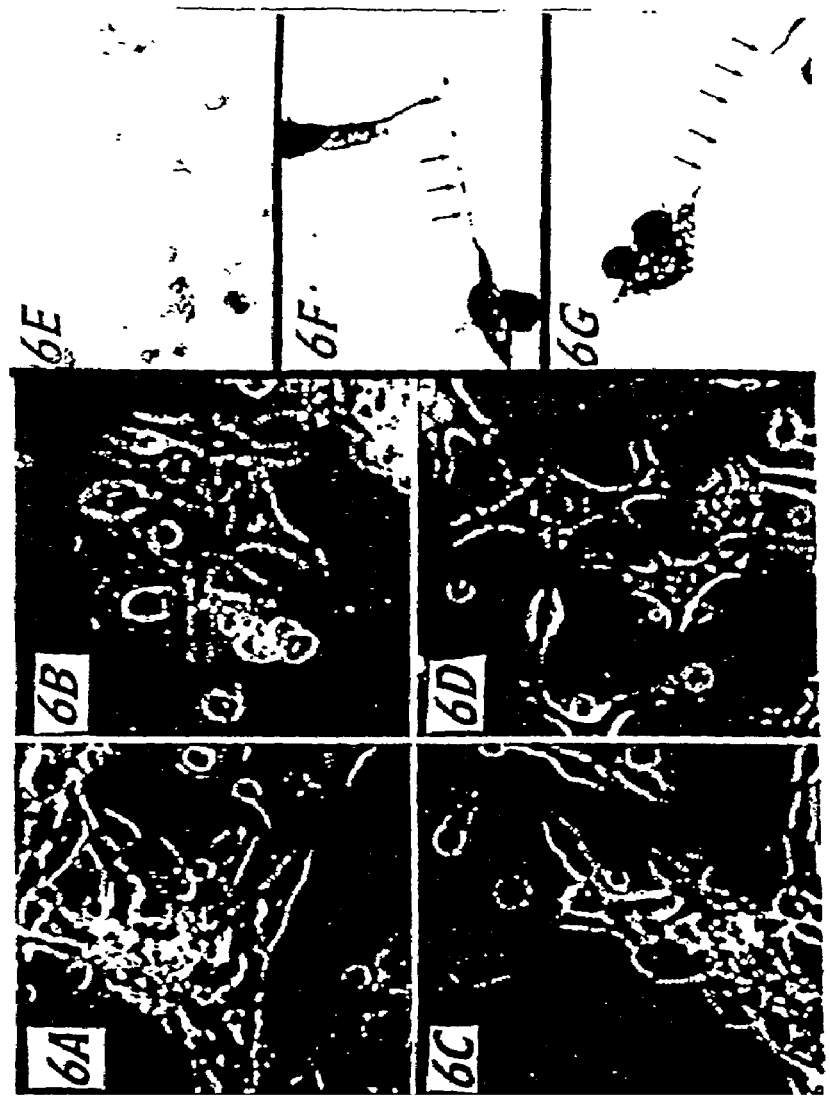

FIGS. 6A–6G show that AD7c-NTP over-expression in transfected neuronal cells results in increased neuritic sprouting. (6A): SH-Sy5y cells stably transfected with pcDNA3 (empty vector). (6B–6D): SH-Sy5y cells stably transfected with pcDNA3-AD7c-NTP. Note fine neuritic processes (arrows) on most cells in FIGS. 6B–6D. Also note lower cell density and numerous round refractile dead cells (arrowheads) in FIG. 6D compared with FIG. 6A. (FIGS. 6E–6G): Immunocytochemical staining of SH-Sy5y cells stably transfected with pcDNA3 (6E) or pcDNA3-AD7c-NTP (6F, 6G) using N3I4 monoclonal antibody. Note intense labeling of perikarya and cell processes (arrows) in 6F and 6G and absent labeling in 6E.

Figures 7A, 7B, 7C:
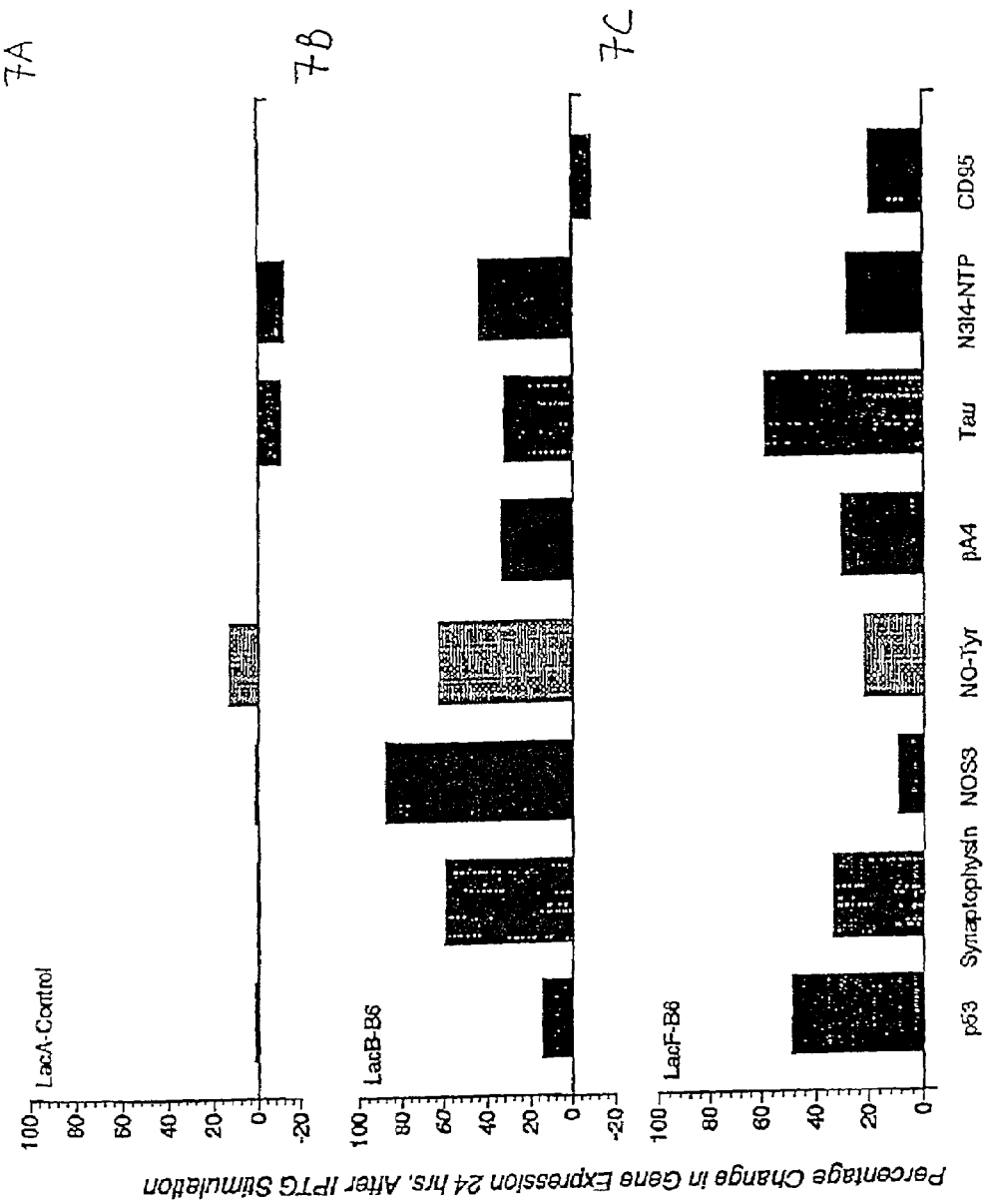
Figures 8A, 8B, 8C, 8D:
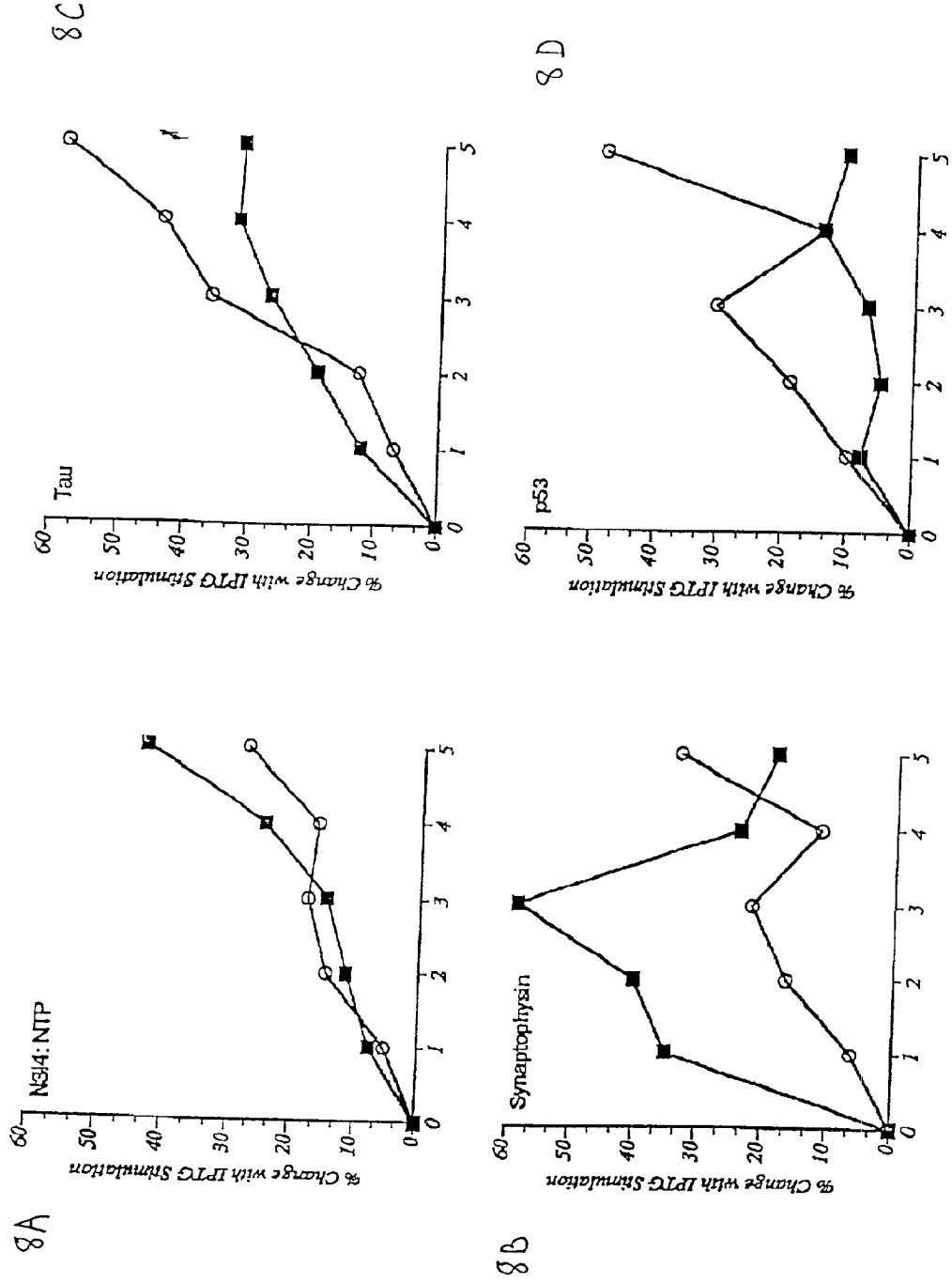

FIGS. 7A–7C depict modulation of gene expression following IPTG induction of AD7c-NTP expression. LacA-control cells (FIG. 7A) lack AD7c-NTP; LacB-B6 cells (FIG. 7B) and LacF-B6 cells (FIG. 7C) are two different clones with different levels of AD7c-NTP induction. Changes in the level of expression 24 hours after induction are indicated for genes involved in AD, neural sprouting, and apoptosis.

FIGS. 8A–8D depict IPTG dose-dependent increases in the level of the NTP (FIG. A), Tau (FIG. B), Synaptophysin (FIG. C) and p53 (FIG. D) proteins. The percent change of the amount of each protein is presented as a function of IPTG concentration (mM).

Figures 9A, 9B:
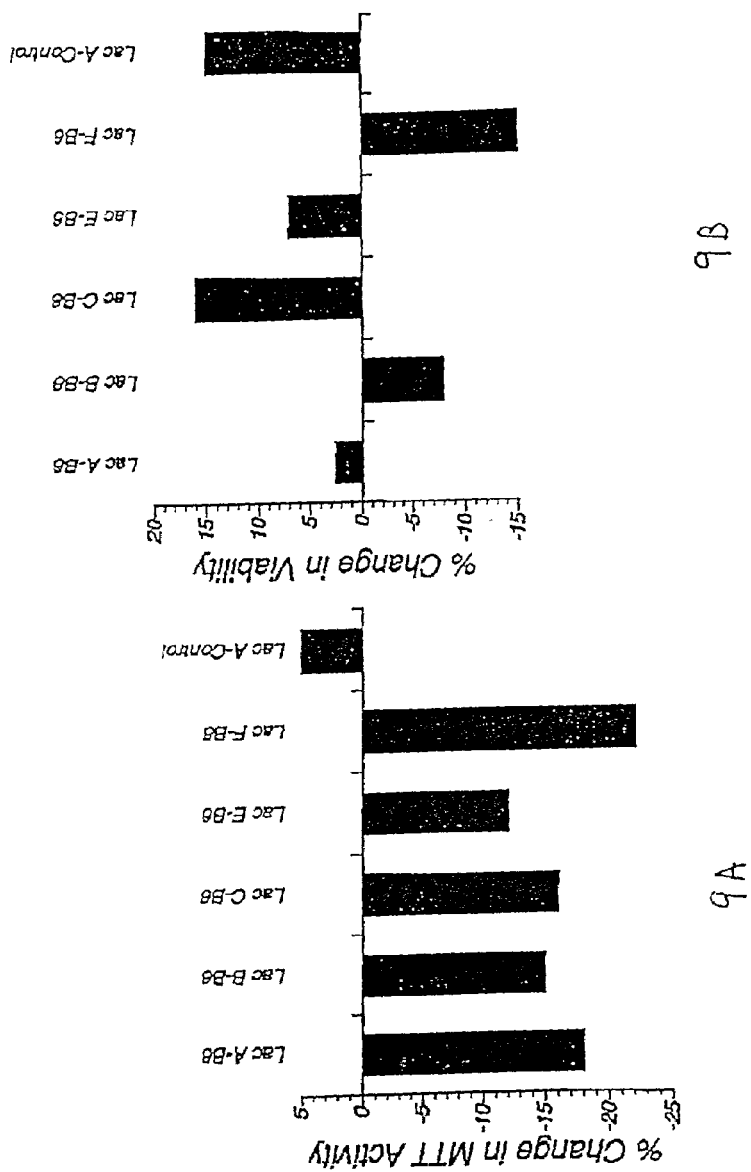

FIGS. 9A and 9B depict the effects of AD7c-NTP expression in CYZ neuronal cells on metabolic (MTT) activity and cell viability. Lac A-Lac F represent six different clones, and B6 indicates AD7c-NTP expression. The percent change for MTT activity (FIG. 9A) and cell viability (FIG. 9B) are indicated for control (Lac A-Control) and AD7c-NTP expressing cell lines.

Figures 10A, 10B:
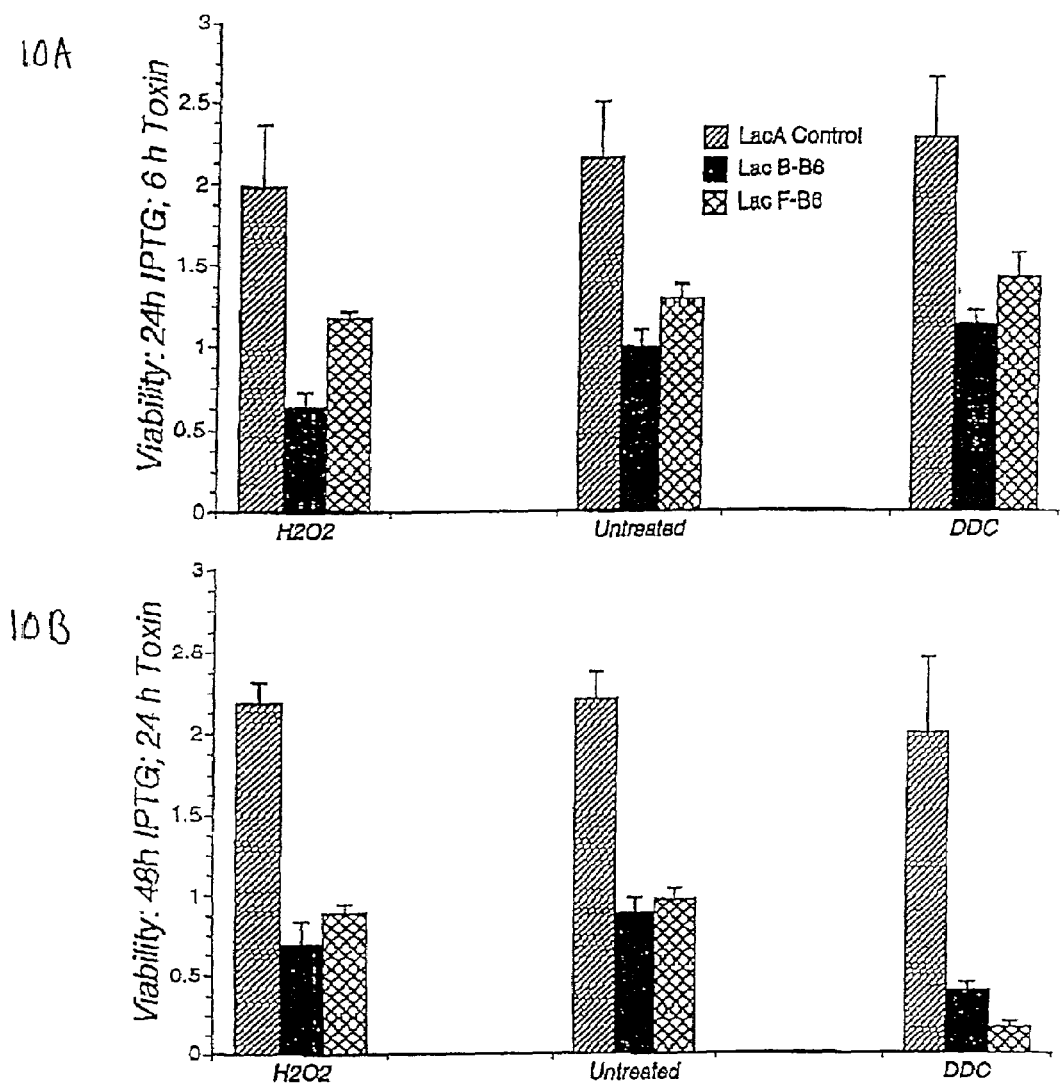

FIGS. 10A and 10B depict the effect of AD7c-NTP expression on cell viability. Nonexpressing Lac A Control and cell lines expressing AD7c-NTP at various levels, Lac B-B6 and Lac F-B6, were assayed for viability after varying exposure time to the protein expression inducing agent (IPTG) and various oxidative stress toxins.

Figure 11:
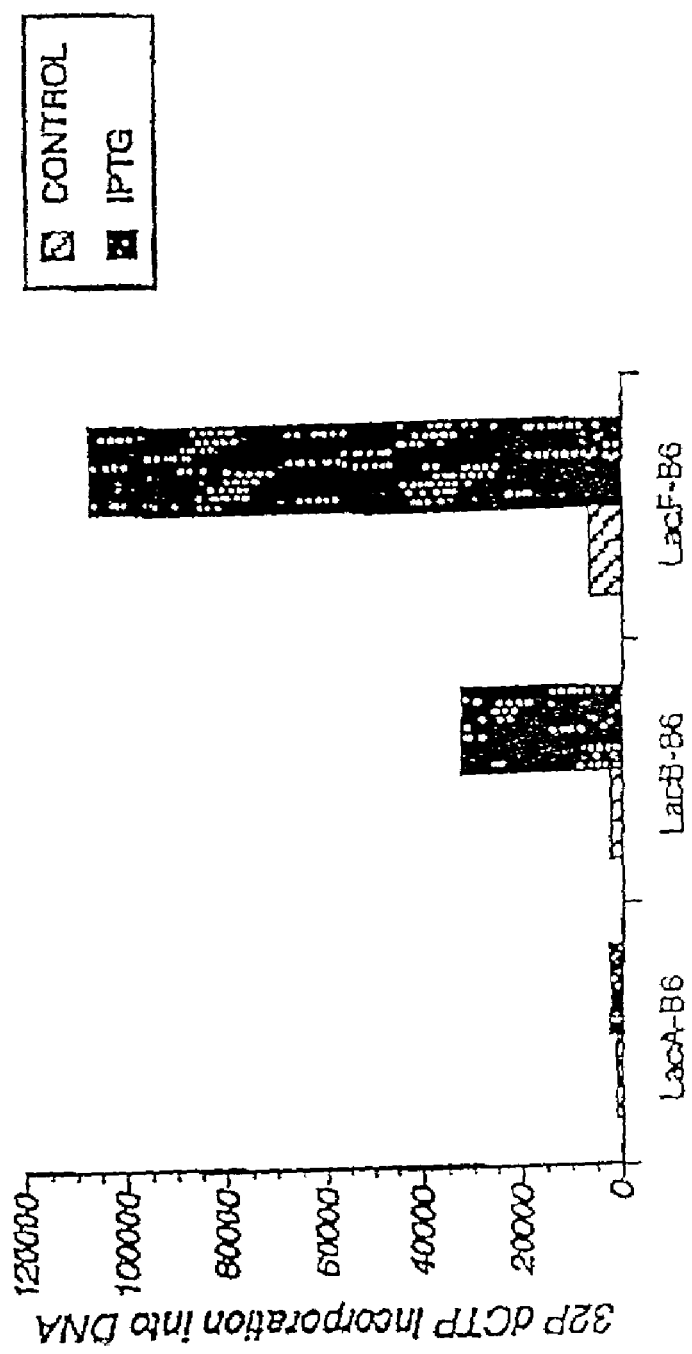

FIG. 11 depicts DNA fragmentation after IPTG induction of AD7c-NTP expression, thereby providing a quantitative assessment of apoptosis. Stably transfected CYZ neuronal cell lines, Lac A, Lac B and Lac F, which express various levels of AD7c-NTP after induction, were incubated in the presence of $^{32}$dCTP label. The amount of radioactive isotope incorporated, under control (uninduced) and IPTG induction conditions, into the respective cell line DNAs is presented.

Figure 12:

FIG. 12 depicts the percent change in viability for cells stably transfected with and expressing AD7c-NTP under conditions that promote and reduce or block oxidative stress.

Agents promoting oxidative stress are the following: hydrogen peroxide (H$_2$O$_2$) diethyldithiocarbamic acid (DDC), S-nitro-N-acetyl-penicillamine (SNAP) and N-acetyl cysteine; and the agent utilized to block or reduce oxidative stress is pygroglutamate (PG).

DETAILED DESCRIPTION OF THE PREFERRED EMBODIMENTS

Definitions

In the description that follows, a number of terms used in recombinant DNA technology are utilized extensively. In order to provide a clear and consistent understanding of the specification and claims, including the scope to be given such terms, the following definitions are provided.

Cloning vector. A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

Expression vector. A vector similar to a cloning vector but which is capable of enhancing the expression of a gene which has been cloned into it, after transformation into a host. The cloned gene is usually placed under the control of (i.e., operably linked to) certain control sequences such as promoter sequences. Promoter sequences may be either constitutive or inducible.

Substantially pure. As used herein means that the desired purified protein is essentially free from contaminating cellular components, said components being associated with the desired protein in nature, as evidenced by a single band following polyacrylamide-sodium dodecyl sulfate gel electrophoresis. Contaminating cellular components may include, but are not limited to, proteinaceous, carbohydrate, or lipid impurities.

The term "substantially pure" is further meant to describe a molecule which is homogeneous by one or more purity or homogeneity characteristics used by those of skill in the art. For example, a substantially pure NTP will show constant and reproducible characteristics within standard experimental deviations for parameters such as the following: molecular weight, chromatographic migration, amino acid composition, amino acid sequence, blocked or unblocked N-terminus, HPLC elution profile, biological activity, and other such parameters. The term, however, is not meant to exclude artificial or synthetic mixtures of the factor with other compounds. In addition, the term is not meant to exclude NTP fusion proteins isolated from a recombinant host.

Recombinant Host. According to the invention, a recombinant host may be any prokaryotic or eukaryotic host cell which contains the desired cloned genes on an expression vector or cloning vector. This term is also meant to include those prokaryotic or eukaryotic cells that have been genetically engineered to contain the desired gene(s) in the chromosome or genome of that organism. For examples of such hosts, see Sambrook et al., *Molecular Cloning: A Laboratory Manual*, Second Edition, Cold Spring Harbor Laboratory, Cold Spring Harbor, N.Y. (1989). Preferred recombinant hosts are neuronal cells transformed with the DNA construct of the invention. Such neuronal cells include brain cells that have been isolated after mechanical disassociation of an animal brain or other available neuronal cell lines.

Recombinant vector. Any cloning vector or expression vector which contains the desired cloned gene(s).

Host Animal. Transgenic animals, all of whose germ and somatic cells contain the DNA construct of the invention. Such transgenic animals are in general vertebrates. Preferred Host Animals are mammals such as non-human primates, mice, sheep, pigs, cattle, goats, guinea pigs, rodents, e.g. rats, and the like. The term Host Animal also includes animals in all stages of development, including embryonic and fetal stages.

Promoter. A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter. According to the invention, preferred promoters are heterologous to the AD7c-NTP gene, that is, the promoters do not drive expression of the gene in a human. Such promoters include the CMV promoter (InVitrogen, San Diego, Calif.), the SV40, MMTV, and hMTIIa promoters (U.S. Pat. No. 5,457,034), the HSV-1 4/5 promoter (U.S. Pat,. No. 5,501,979), and the early intermediate HCMV promoter (WO92/17581). Also, it is preferred that the promoter is neuro-specific, that is, it is induced selectively in neuronal tissue. Also, neuro-specific enhancer elements may be employed. Examples of neuro-specific promoters include but are not limited to the promoter which controls the neurofilament gene (WO91/02788; Byrne and Ruddle, *Proc. Natl. Acad. Sci. USA* 86:5473–5477 (1989)), the neuron specific promoter of the human neurofilament light gene (NFL) (U.S. Pat. No. 5,569,827); the promoter of the β2-subunit of the neuronal nicotinic acetylcholine receptor (EP 0 171 105; U.S. application Ser. No. 08/358,627), the hThy-1 promoter (WO95/03397; U.S. application Ser. No. 08/096,944; Gordon, J. et al., *Cell* 50:445–452 (1987)); the Tα1 α-tubulin promoter (WO95/25795; U.S. application Ser. No. 08/215,083; Gloster et al., *J. Neurosci.* 14:7319–7330 (1994)), the APP promoter, the rat neuron specific promoter, the human β actin gene promoter, the human platelet derived growth factor B (PDGF-B) chain gene promoter, the rat sodium channel gene promoter, the mouse myelin basic protein gene promoter, the human copper-zinc superoxide dismutase gene promoter, mammalian POU-domain regulatory gene promoter (WO93/14200; U.S. application Ser. Nos. 07/817,584 and 07/915,469); human platelet derived growth factor B (PDGF-B) chain gene promoter (WO96/40895 ; U.S. application Ser. Nos. 08/486,018 and 08/486,538; Sasahara et al., *Cell* 64:217–227 (1991)); and the neuron-specific enolase promoter (McConlogue et al., *Aging* 15:S12 (1994); Higgins et al., *Ann Neurol.* 35:598–607 (1995); Mucke et al., *Brain Res.* 666:151–167 (1994); Higgins et al., *Proc. Natl. Acad. Sci USA* 92:4402–4406 (1995); WO96/40896; U.S. application Ser. No. 08/480,653; and U.S. Pat. No. 5,387,742); and sequences that regulate the oligodendroglial-specific expression of JC virus, glial-specific expression of the proteolipid protein, and the glial fibrillary acidic protein genes (U.S. Pat. No. 5,082,670). Other neuro-specific promoters will be readily apparent to those of skill in the art. Since protein phosphorylation is critical for neuronal regulation (Kennedy, "Second Messengers and Neuronal Function," in *An Introduction to Molecular Neurobiology*, Hall, Ed., Sinauer Associates, Inc. (1992)), protein kinase promoter sequences can be used to achieve sufficient levels of NTP gene expression.

Gene. A DNA sequence that contains information needed for expressing a polypeptide or protein.

Structural gene. A DNA sequence that is transcribed into messenger RNA (mRNA) that is then translated into a sequence of amino acids characteristic of a specific polypeptide.

Antisense RNA gene/Antisense RNA. In eukaryotes, mRNA is transcribed by RNA polymerase II. However, it is also known that one may construct a gene containing a RNA polymerase II template wherein a RNA sequence is transcribed which has a sequence complementary to that of a specific mRNA but is not normally translated. Such a gene construct is herein termed an "antisense RNA gene" and such a RNA transcript is termed an "antisense RNA." Antisense RNAs are not normally translatable due to the presence of translation stop codons in the antisense RNA sequence.

Antisense oligonucleotide. A DNA or RNA molecule or a derivative of a DNA or RNA molecule containing a nucleotide sequence which is complementary to that of a specific mRNA. An antisense oligonucleotide binds to the complementary sequence in a specific mRNA and inhibits translation of the mRNA. There are many known derivatives of such DNA and RNA molecules. See, for example, U.S. Pat. Nos. 5,602,240, 5,596,091, 5,506,212, 5,521,302, 5,541,307, 5,510,476, 5,514,787, 5,543,507, 5,512,438, 5,510,239, 5,514,577, 5,519,134, 5,554,746, 5,276,019, 5,286,717, 5,264,423, as well as WO96/35706, WO96/32474, WO96/29337 (thiono triester modified antisense oligodeoxynucleotide phosphorothioates), WO94/17093 (oligonucleotide alkylphosphonates and alkylphosphothioates), WO94/08004 (oligonucleotide phosphothioates, methyl phosphates, phosphoramidates, dithioates, bridged phosphorothioates, bridge phosphoramidates, sulfones, sulfates, ketos, phosphate esters and phosphorobutylamines (van der Krol et al., *Biotech.* 6:958–976 (1988); Uhlmann et al., *Chem. Rev.* 90:542–585 (1990)), WO94/02499 (oligonucleotide alkylphosphonothioates and arylphosphonothioates), and WO942/20697 (3'-end capped oligonucleotides). Particular NTP antisense oligonucleotides of the present invention include derivatives such as S-oligonucleotides (phosphorothioate derivatives or S-oligos, see, Jack Cohen, *Oligodeoxynucleotides, Antisense Inhibitors of Gene Expression*, CRC Press (1989)). S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention may be prepared by treatrnent of the corresponding O-oligos with 3H-1,2-benzodithiol-3-one-1,1-dioxide which is a sulfur transfer reagent. See Iyer et al., *J. Org. Chem.* 55:4693–4698 (1990); and Iyer et al., *J. Am. Chem. Soc.* 112:1253–1254 (1990).

Antisense Therapy. A method of treatment wherein antisense oligonucleotides are administered to a patient in order to inhibit the expression of the corresponding protein.

Complementary DNA (cDNA). A "complementary DNA," or "CDNA" gene includes recombinant genes synthesized by reverse transcription of mRNA and from which intervening sequences (introns) have been removed.

Expression. Expression is the process by which a polypeptide is produced from a structural gene. The process involves transcription of the gene into mRNA and the translation of such mRNA into polypeptide(s).

Homologous/Nonhomologous Two nucleic acid molecules are considered to be "homologous" if their nucleotide sequences share a similarity of greater than 40%, as determined by HASH-coding algorithms (Wilber, W. J. and Lipman, D. J., *Proc. Natl. Acad. Sci.* 80:726–730 (1983)). Two nucleic acid molecules are considered to be "nonhomologous" if their nucleotide sequences share a similarity of less than 40%.

Ribozyme. A ribozyme is an RNA molecule that contains a catalytic center. The term includes RNA enzymes, self-splicing RNAs, and self-cleaving RNAs.

Ribozyme Therapy. A method of treatment wherein ribozyme is administered to a patient in order to inhibit the translation of the target mRNA.

Fragment. A "fragment" of a molecule such as NTP is meant to refer to any polypeptide subset of that molecule.

Functional Derivative. The term "functional derivatives" is intended to include the "variants," "analogues," or "chemical derivatives" of the molecule. A "variant" of a molecule such as NTP is meant to refer to a naturally occurring molecule substantially similar to either the entire molecule, or a fragment thereof. An "analogue" of a molecule such as NTP is meant to refer to a non-natural molecule substantially similar to either the entire molecule or a fragment thereof.

A molecule is said to be "substantially similar" to another molecule if the sequence of amino acids in both molecules is substantially the same, and if both molecules possess a similar biological activity. Thus, provided that two molecules possess a similar activity, they are considered variants as that term is used herein even if one of the molecules contains additional amino acid residues not found in the other, or if the sequence of amino acid residues is not identical.

As used herein, a molecule is said to be a "chemical derivative" of another molecule when it contains additional chemical moieties not normally apart of the molecule. Such moieties may improve the molecule's solubility, absorption, biological half-life, etc. The moieties may alternatively decrease the toxicity of the molecule, eliminate or attenuate any undesirable side effect of the molecule, etc. Examples of moieties capable of mediating such effects are disclosed in *Remington's Pharmaceutical Sciences* (1980) and will be apparent to those of ordinary skill in the art.

AD7c-NTP. The term "AD7c-NTP" refers to the protein having sequence ID No. 2 as well as allelic variants thereof.

We have isolated a cDNA designated AD7c-NTP, that is expressed in neurons, and over-expressed in brains with AD. The 1442-nucleotide kD7c-NTP cDNA encodes a ~41 kD membrane spanning protein that has a hydrophobic leader sequence and myristylation motif near the amino terminus. The AD7c-NTP cDNA is an Alu sequence-containing gene with three regions of significant homology to the alternatively spliced A4 form of NF2, the β1 subunit of integrin, human integral membrane protein, myelin oligoglycoprotein-16 precursor, and human decay accelerating factor 2 precursor, and two regions with significant homology with sequences in the Huntington's disease region on Chromosome 4p16.3. Expression of AD7c-NTP was confirmed by nucleic acid sequencing of RT-PCR products isolated from brain. AD7c-NTP cRNA probes hybridized with 1.4 kB and 0.9 kB mRNA transcripts by Northern blot analysis, and monoclonal antibodies generated with the recombinant protein were immunoreactive with ~39–45 kD and ~19–21 kD molecules by Western blot analysis of human brain. Quantitation of data obtained from 17 AD and 11 age-matched control brains demonstrated significantly higher levels of AD7c-NTP expression in AD. In situ hybridization and immunostaining studies localized AD7c-NTP gene expression in neurons, and confirmed the over-expression associated with AD neurodegeneration. Increased AD7c-NTP protein levels were also detectable in cerebrospinal fluid by Western blot analysis. The results suggest that abnormal AD7c-NTP gene expression is associated with AD neurodegeneration. Thus, abnormal expression of AD7c-NTP is a phenotype associated with Atzheimer's disease.

The confirmation that AD7c-NTP expression leads to Alzheimer's disease led to the expectation that transgenic animals and cell lines which over express the AD7c-NTP can be used to screen drugs for use in the treatment or prevention of Alzheimer's disease, neuroectodermal tumors, malignant astrocytomas and glioblastomas.

The invention relates to a DNA construct, wherein said DNA, construct comprises a DNA molecule of Seq. ID No. 1, or a fragment thereof, or a DNA molecule which is at least 40% homologous thereto, more preferably, at least 85% homologous thereto, most preferably, at least 90% homoloyous thereto. Preferably, the DNA construct encodes AD7c-NTP having Seq. ID No. 2. Also preferably, the DNA sequence is under control of a heterologous neuro-specific promoter. Examples of promoters that can be used to drive expression of AD7c-NTP in a host cell are described above. Having the promoter in hand, one may simply ligate the promoter to the DNA molecule of Seq. ID No. 1. Methods for ligating DNA fragments are well known to those of ordinary skill in the art. Preferably, the DNA molecule having Seq. ID No. 1 is ligated to a plasmid which contains the promoter and which results in the promoter being in operable linkage to the AD7c-NTP DNA sequence.

Fragments of the DNA molecule of the invention code for proteins having the activity of AD7c-NTP, that is, the DNA fragments induce neutitic sprouting, nerve cell death, nerve cell degeneration, neurofibrillary tangles, and/or irregular swollen neurites in a host which expresses the fragment. Such hosts include cellular hosts and transgenic animals.

DNA molecules which are at least 40%, 85% or 90% homologous Seq. ID No. 1 may be isolated from cDNA libraries of humans and animals by hybridization under stringent conditions to the DNA molecule gf Seq. ID No. 1 according to methods known to those of skill in the art. Stringent hybridization conditions are employed which select for DNA molecules having at least 40%, 85% and 90% homology to Seq. ID No. 1 are described in Sambrook et al., In: *Molecular Cloning, A Laboratory Manual*, Cold Spring Harbor Laboratory Press, Cold Spring Harbor, N.Y. (1989); and Maniatis et al., *Molecular Cloning—A Laboratory Manual*, Cold Spring Harbor Laboratory, Cold Spring Harbor, N.Y., 1985. The hybridizations may be carried out in 6×SSC/5×Denhardt's solution/0.1% SDS at 65° C. The degree of stringency is determined in the washing step. Thus, suitable conditions include 0.2×SSC/0.01% SDS/65° C. and 0.1×SSC/0.01% SDS/65° C.

The invention also relates to cells containing the DNA construct of the invention. Examples of suitable cells that may contain the DNA construct of the invention include eukaryotic and prokaryotic cells. Preferred are eukaryotic cells such as those derived from a vertebrate animal including human cells, non-human primate cells, porcine cells, ovine cells and the like. Further, it is contemplated that the cell line may be a neuronal cell line from one of these vertebrate animals. Examples of such cell lines include SH-Sy5y, pNET-1, pNET-2, hNTs (Stratagene, Inc.), and A172 (ATCC) neuronal cells. See O'Barr, S. et al., *Neurobiol. Aging* 17:131–136 (1996); Ozturk, M. et al., *Proc. Natl.* *Acad. Sci. USA* 86:419–423 (1989); Bieldler, et al., *Cancer Res.* 33:2643–2652 (1973); and The et al.,*Nature Genet.* 3:2643–2652 (1993).

Methods for introducing DNA constructs into cells in vitro, in vivo and ex vivo are well known to those of ordinary skill in the art. See, for example, U.S. Pat. Nos. 5,595,899, 5,521,291, 5,166,320, 5,547,932, 5,354,844, 5,399,346, WO94/10569 and Citron et al., *Nature* 360: 622–674 (1995).

The invention also relates to transgenic non-human animals which comprise the DNA construct of the invention in each of its germ and somatic cells and which over express AD7c-NTP. Such transgenic animals may be obtained, for example, by injecting the DNA construct of the invention into a fertilized egg which is allowed to develop into an adult animal. To prepare a transgenic animal, a few hundred DNA molecules are injected into the pro-nucleus of a fertilized one cell egg. The micro injected eggs are then transferred into the oviducts of pseudopregnant foster mothers and allowed to develop. It has been. reported by Brinster et al., *Proc. Natl. Acad. Sci. USA* 82:4438–4442 (1985), that about 25% of mice which develop will inherit one or more copies of the micro injected DNA. Alternatively, the transgenic animals may be obtained by utilizing recombinant ES cells for the generation of the transgenes, as described by Gossler et al., *Proc. Natl. Acad. Sci. USA* 83:9065–9069 (1986). The offspring may be analyzed for the integration of the transgene by isolating genomic DNA from tail tissue and the fragment coding for AD7c-NTP identified by conventional DNA-hybridization techniques (Southern, *J. Mol. Biol.* 98:503–517 (1975)). Animals positive for the AD7c-NTP gene are further bred to expand the colonies of AD7c-NTP mice. General and specific examples of methods of preparing transgenic animals are disclosed in U.S. Pat. Nos. 5,602,299, 5,366,894, 5,464,758, 5,569,827, WO96/40896 (U.S. application Ser. No. 08/480,653); WO96/40895 (U.S. application Ser. Nos. 08/486,018 and 08/486,536); WO943/14200 (U.S. application Ser. Nos. 07/817,584 and 07/915, 469); WO95/03397 (U.S. application Ser. No. 08/096,944); WO95/25792 (U.S. application Ser. No. 08/215,083); EP 0 717 105 (U.S. application Ser. No. 08/358,627); and Hogan et al., *Manipulating the Mouse Embryo*, Cold Spring Harbor Laboratory, Cold Spring Harbor, N.Y., 1986); Hammer et al., *Cell* 63:1099–1112(1990).

Once obtained, the transgenic animals which contain the AD7c-NTP may be analyzed by imrnmunohistology for evidence of AD7c-NTP expression as well as for evidence of neuronal or neuritic abnormalities associated with Al zheimer's disease, neuroectodermal tumors, malignant astrocytomas and glioblastomas. Sections of the brains may be stained with antibodies specific for AD7c-NTP, either monoclonal or polyclonal.

The invention also relates to an in vitro method for screening candidate drugs that are potentially useful for the treatment or prevention of Alzheimer's disease, neuroectodermal tumors, malignant astrocytomas, and glioblastomas, which comprises (a) contacting a candidate drug with a host transfected with a DNA construct, wherein the DNA construct comprises a DNA molecule of Seq. ID No. 1 or a DNA molecule that is at least 90% homologous thereto, and wherein said host over expresses the protein coded for by said DNA molecule, and (b) detecting at least one of the following:

(i) the suppression or prevention ofexpression of the protein;

(ii) the increased degradation of the protein; or (iii) the reduction of frequency of at least one of neuritic sprouting, nerve cell death, degenerating neurons, neurofibrillary tangles, or irregular swollen neurites and axons in the host;

due to the drug candidate.

In a preferred embodiment, the host is a transgenic animal. In another preferred embodiment, the host is a cell in vitro. The suppression or prevention of expression, and the increased degradation of the protein such as AD7c-NTP may be detected with antibodies specific for AD7c-NTP. Monoclonal and polyclonal antibodies which are specific for AD7c-NTP as well as methods for the qualitative and quantitative detection of AD7c-NTP are described herein as well as in WO94/23756 and U.S. application Ser. No. 08/340,426. Such testing may be carried out on CSF of the transgenic animal or by immunohistochemical staining of a tissue section from the brain of the animal. In addition, such testing may be carried out by Western blot analysis, ELISA or RIA.

Immunohistochemical staining may also be carried out to determine the frequency of at least one of neuritic sprouting, nerve cell death, degenerating neurons, neurofibrillary tangles, or irregular swollen neurites and axons in the animal. Since in general the animal will have to be sacrificed, a pool of test and control transgenic animals should be tested. After sacrifice, the relative frequency of neuritic sprouting, nerve cell death, degenerating neurons, neurofibrillary tangles, or irregular swollen neurites and axons is determined for both groups. If the test group exhibits a reduced frequency of neuritic sprouting, nerve cell death, degenerating neurons, neurofibrillary tangles, or irregular swollen neurites and axons, the drug may be considered promising for the treatment or prevention of Alzheimer's disease, neuroectodermal tumors, malignant astrocytomas, or glioblastomas.

When the host is a transgenic animal, the effect of a drug candidate may also be tested by behavioral tests which are designed to assess learning and memory deficits. An example of such a test is the Morris water maze disclosed by Morris, *Learn Motivat.* 12:239–260 (1981) and WO96/40895.

In the practice of the method of the invention, the candidate drug is administered to the transgenic animals or introduced into the culture media of cells derived from the animals or cells transfected with the DNA construct of the invention. The candidate drug may be administered over a period of time and in various dosages, and the animals or animal cells tested for alterations in AD7-cNTP expression, nerve cell degradation or histopathology. In case of transgenic animals, they may also be tested for improvement in behavior tests.

When cells are to be tested in vitro for the effect of the candidate drug, they are grown in a growth conducive medium and the medium replaced with a media containing the candidate drug. Wide varieties of medias which promote growth of practically any cell type are commercially available, for example, from Life Technologies, Inc. (Gaithersburg, Md.). If the candidate drug is only sparingly soluble in the media, a stock solution may be prepared in dimethyl sulfoxide (DMSO). The DMSO solution is then admixed with the media. Preferably, the DMSO concentration in the media does not exceed 0.5%, preferably, 0.1%. The cells are then incubated in the presence of the drug-containing media for a preselected time period (e.g. 2–10 hours) at a preselected temperature, for example, about 37° C. At the end of this time period, the media may again be removed and fresh media containing the candidate drug is added. The cells are then incubated for a second preselected time period (e.g. 2–16 hours). This procedure can be repeated as necessary to achieve a significant result.

After the treatment period, the cells are tested either for the level of NTP expression and/or, if the cells are neuronal cells, examined for the presence and/or frequency of neuritic sprouting, nerve cell death, degenerating neurons, neurofibrillary tangles, or irregular swollen neurites and axons. In order to test for the level of NTP expression, immunohistochemical staining may be carried out as described in the Examples. Alternatively, the plates containing the cells may be centrifuged to pellet cellular debris from the medium, and a sample of the media tested for the NTP concentration. The concentration of NTP may be determined by ELISA with an antibody which is specific for NTP. Methods for carrying out such assays are disclosed in WO94/10569 and are well known to those of ordinary skill in the art. The concentration of NTP in the test cells/media is then compared to the concentration of control cells that have been treated the same way except that the media does not contain the candidate drug (but may contain the same level of DMSO). The results of the ELISA are fit to a standard curve and expressed as ng/mL NTP. See WO96/40895.

In a preferred in vitro model system, the AD7c-NTP is cloned into a Lac-Switch inducible system and stably transfected into neuronal cells (e.g., PNET2 (CYZ), SH-Sy5y and hNT2). AD7c-NTP may be the full length cDNA or a CAT reporter gene construct. Protein expression is inducible with 1–5 mM IPTG. Cultures may be examined for cell death, neuritic sprouting and the corresponding changes in gene expression associated with these or other AD-related phenomena. Analytical methods available for analysis include, but are not limited to, viability (Crystal violet) and metabolic (MTT) assays, western blot and immunocytochemical staining, Microtiter ImmunoCytochemical ELISA (MICE) assay, apoptosis DNA fragmentation assays (ladder, end-labeling, Hoechst staining and TUNEL assay) and CAT assay for gene expression studies.

The effects of candidate drugs on the toxicity of NTP to neuronal cells can also be determined in primary rat cortical cell cultures according to WO96/40895, or with human fetal brain tissue, or differentiated neuronal cell lines such as hNT2 and SH-Sy5y cell lines. Alternatively, neuronal cells transformed with and expressing the gene coding for AD7c-NTP as described herein may be used.

Antisense oligonucleotides have been described as naturally occurring biological inhibitors of gene expression in both prokaryotes (Mizuno et al., *Proc. Natl. Acad. Sci. USA* 81:1966–1970 (1984)) and eukaryotes (Heywood, *Nucleic Acids Res.* 14:6771–6772 (1986)), and these sequences presumably function by hybridizing to complementary mRNA sequences, resulting in hybridization arrest of translation (Paterson, et al., *Proc. Natl. Acad. Sci. USA,* 74:4370–4374 (1987)).

Antisense oligonucleotides are short synthetic DNA or RNA nucleotide molecules formulated to be complementary to a specific gene or RNA message. Through the binding of these oligomers to a target DNA or mRNA sequence, transcription or translation of the gene can be selectively blocked and the disease process generated by that gene can be halted (see, for example, Jack Cohen, *Oligodeoxynucleotides, Antisense Inhibitors of Gene Expression,* CRC Press (1989)). The cytoplasmic location of mRNA provides a target considered to be readily accessible to antisense oligodeoxynucleotides entering the cell; hence much of the work in the field has focused on RNA as a target. Currently, the use of antisense oligodeoxynucleotides provides a useful tool for exploring regulation of gene expression in vitro and in tissue culture (Rothenberg, et al., *J. Natl. Cancer Inst.* 81:1539–1544 (1989)).

Antisense therapy is the administration of exogenous oligonicleotides which bind to a target polynucleotide located within the cells. For example, antisense oligonucleotides may be administered systemically for anticancer therapy (WO 90/09180). AD7c-NTP is produced by neuroectodermal tumor cells, malignant astrocytoma cells, glioblastoma cells, and in relatively high concentrations (i.e, relative to controls) in brain tissue of AD patients. Thus, AD7c-NTP antisense oligonucleotides of the present invention may be active in treatment against AD, as well as neuroectodermal tumors, malignant astrocytomas, and glioblastomas.

As discussed above, the invention also relates to the correct amino acid and nucleotide sequence for NTP. Thus, the invention also relates to antisense oligonucleotides which are complementary to the mRNA which may be transcribed from Seq. ID No. 1, wherein said oligonucleotides correspond to regions of the NTP gene that were incorrectly sequenced in WO94,/23756 and WO96/15272, e.g. in the region including nucleotides 150–1139 (nucleotides 1–148 of FIG. 16R of published application; nucleotides 1–149 of Seq. ID No. 1 of the present application: were correctly sequenced). This incorrect sequence is present in Seq. ID Nos. 3 and 4. Thus, the invention relates to an antisense oligonucleotide which is complementary to an NTP mRNA sequence corresponding to nucleotides 150–1139 of Seq. ID No, 1. Preferebly, the oligonucleotides correspond to regions including nucleotides selected from the group consisting of nucleotides 150, 194–195, 240–241, 243, 244, 255–256, 266–267, 269–271, 276, 267, 279–280, 293–295, 338–340, 411, 459, 532–533, 591, 633–644, 795–797, 828, 853–854, 876–877, 883, 884–885, 898, 976, 979–980, 999, 1037, 1043–1044, 1092–1096, 1099, and 1116–1119 of Seq. ID No. 1. More preferably, the invention is related to an antisense oligonucleotide sequence selected from the group consisting of: 5' TTC ATC CTG GGT AAG AGT GGG ACA CCT GTG (Seq. ID No. 9); 5' TGG TGC ATG TCT TTG GTC CCA GCT AC (Seq ID No. 10)); and 5' ATC AAC CTG GCG AAC ATG GTG AAC CCC ATC (Seq. ID No. 11).

Also preferably, the sequence is a 15 to 40-mer, more preferably, a 15 to 30-mer. Also preferably, the antisense oligonucleotide it a phosphoriothioate or one of the other oligonucleotide derivatives mentioned above. Also preferred are antisense oligonucleotides which are complementary to an NTP nucleic acid sequence and which are nonhomologous to PTP nucleic acid sequences and that correspond to regions that were incorrectly sequenced in the past, as well as pharmaceutical compositions comprising such oligonucleotides and a pharmaceutically acceptable carrier.

Included as well in the present invention are pharmaceutical compositions comprising an effective amount of at least one of the NTP antisense oligonucleotides of the invention in combination with a pharmaceutically acceptable carrier. In one embodiment, a single NTP antisense oligonucleotide is utilized. In another embodiment, two NTP antisense oligonucleotides are utilized which are complementary to adjacent regions of the NTP DNA. Administration of two NTP antisense oligonucleotides which are complementary to adjacent regions of the DNA or corresponding mRNA may allow for more efficient inhibition of NTP genomic transcription or mRNA translation, resulting in more effective inhibition of NTP production.

Preferably, the NTP antisense oligonucleotide is coadministered with an agent which enhances the uptake of the antisense molecule by the cells. For example, the NTP antisense oligonucleotide may be combined with a lipophilic cationic compound which may be in the form of liposomes. The use of liposomes to introduce nucleotides into cells is taught, for example, in U.S. Pat. Nos. 4,897,355 and 4,394,448. See also U.S. Pat. Nos. 4,235,871, 4,231,877, 4,224,179, 4,753,788, 4,673,567, 4,247,411, 4,814,270 for general methods of preparing liposomes comprising biological materials.

Alternatively, the NTP antisense oligonucleotide may be combined with a lipophilic carrier such as any one of a number of sterols including cholesterol, cholate and deoxycholic acid. A preferred sterol is cholesterol.

In addition, the NTP antisense oligonucleotide may be conjugated to a peptide that is ingested by cells. Examples of useful peptides include peptide hormones, antigens or antibodies, and peptide toxins. By choosing a peptide that is selectively taken up by the neoplastic cells, specific delivery of the antisense agent may be effected. The NTP antisense oligonucleotide may be covalently bound via the 5'OH group by formation of an activated aminoalkyl derivative. The peptide of choice may then be covalently attached to the activated NTP antisense oligonucleotide via an amino and sulfhydryl reactive hetero bifunctional reagent. The latter is bound to a cysteine residue present in the peptide. Upon exposure of cells to the NTP antisense oligonucleotide bound to the peptide, the peptidyl antisense agent is endocytosed and the NTP antisense oligonucleotide binds to the target NTP mRNA to inhibit translation (Haralambid et al., WO 8903849; Lebleu et al., EP 0263740).

The NTP antisense oligonucleotides and the pharmaceutical compositions of the present invention may be administered by any means that achieve their intended purpose. For example, administration may be by parenteral, subcutaneous, intravenous, intramuscular, intra-peritoneal, transdermal, intrathecal or intracranial routes. The dosage administered will be dependent upon the age, health, and weight of the recipient, kind of concurrent treatment, if any, frequency of treatment, and the nature of the effect desired.

Compositions within the scope of this invention include all compositions wherein the NTP antisense oligonucleotide is contained in an amount effective to achieve inhibition of proliferation and/or stimulate differentiation of the subject cancer cells, or alleviate AD. While individual needs vary, determination of optimal ranges of effective amounts of each component is with the skill of the art. Typically, the NTP antisense oligonucleotide may be administered to mammals, e.g. humans, at a dose of 0.005 to 1 mg/kg/day, or an equivalent amount of the pharmaceutically acceptable salt thereof, per day of the body weight of the mammal being treated.

Antisense oligonucleotides can be prepared which are designed to interfere with transcription of the NTP gene by binding transcribed regions of duplex DNA (including introns, exons, or both) and forming triple helices (U.S. Pat. Nos. 5,594,121, 5,591,607, WO96/35706, WO96/32474, WO94/17091, WO94/01550, WO 91/06626, WO 92/10590). Preferred oligonucleotides for triple helix formation are oligonucleotides which have inverted polarities for at least two regions of the oligonucleotide (Id.). Such oligonucleotides comprise tandem sequences of opposite polarity such as 3'---5'-L-5'---3', or 5'---3'-L-3'---5', wherein L represents a 0–10 base oligonucleotide linkage between oligonucleotides. The inverted polarity form stabilizes single-stranded oligonucleotides to exonuclease degradation (Froehler et al., supra). Preferred oligonucleotides are nonhomologous to PTP nucleic acid sequences, and correspond to regions that were incorrectly sequenced in the past. The invention is related as well to pharmaceutical compositions comprising such oligodeoxynucleotides and a pharmaceutically acceptable carrier.

In therapeutic application, the triple helix-forming oligonucleotides can be formulated in pharmaceutical preparations for a variety of modes of administration, including systemic or localized administration, as described above.

The antisense oligonucleotides and triple helix-forming oligonucleotides of the present invention may be prepared according to any of the methods that are well known to those of ordinary skill in the art, including methods of solid phase synthesis and other methods as disclosed in the publications, patents and patent applications cited herein.

The invention is also directed to ribozymes comprising a target sequence which is complementary to an NTP sequence of Seq. ID So. 1 and nonhomologous to PTP nucleic acid sequences and that correspond to regions that were incorrectly sequenced in the past, as well as pharmaceutical compositions comprising such ribozymes and a pharmaceutically acceptable carrier.

Ribozymes provide an alternative method to inhibit mRNA function. Ribozymes may be RNA enzymes, self-splicing RNAs, and self-cleaving RNAs (Cech et al., *Journal of Biological Chemistry* 267:17479–17482 (1992)). It is possible to construct de novo ribozymes which have an endonuclease activity directed in trans to a certain target sequence. Since these ribozymes can act on various sequences, ribozymes can be designed for virtually any RNA substrate. Thus, ribozymes are very flexible tools for inhibiting the expression of specific genes and provide an alternative to antisense constructs.

A ribozyme against chloramphenicol acetyltransferase mRNA has been successfully constructed (Haseloff et al., *Nature* 334:585–591 (1988); Uhlenbeck et al., *Nature* 328: 596–600 (1987)). The ribozyme contains three structural domains: 1) a highly conserved region of nucleotides which flank the cleavage site in the 5' direction; 2) the highly conserved sequences contained in naturally occurring cleavage domains of ribozymes, forming a base-paired stem; and 3) the regions which flank the cleavage site on both sides and ensure the exact arrangement of the ribozyme in relation to the cleavage site and the cohesion of the substrate and enzyme. RNA enzymes constructed according to this model have already proved suitable in vitro for the specific cleaving of RNA sequences (Haseloff et al., supra). Examples of such regions include the antisense oligonucleotides mentioned above.

Alternatively, hairpin ribozymes may be used in which the active site is derived from the minus strand of the satellite RNA of tobacco ring spot virus (Hampel et al., *Biochemistry* 28:4929–4933 (1989)). Recently, a hairpin ribozyme was designed which cleaves human immunodeficiency virus type 1 RNA (Ojwang et al., *Proc. Natl. Acad. Sci. USA* 89:10802–10806 (1992)). Other self-cleaving RNA activities are associated with hepatitis delta virus (Kuo et al., *J. Virol.* 62:4429–4444 (1988)). See also U.S. Pat. No. 5,574, 143 for methods of preparing and using ribozymes. Preferably, the NTP ribozyme molecule of the present invention is designed based upon the chloramphenicol acetyltransferase ribozyme or hairpin ribozymes, described above. Alternatively, NTP ribozyme molecules are designed as described by Eckstein et al. (International Publication No. WO 92/07065) who disclose catalytically active ribozyme constructions which have increased stability against chemical and enzymatic degradation, and thus are useful as therapeutic agents.

In an alternative approach, an external guide sequence (EGS) can be constructed for directing the endogenous ribozyme, RNase P, to intracellular NTP mRNA, which is subsequently cleaved by the cellular ribozyme (Altman et al., U.S. Pat. No. 5,168,053). Preferably, the NTP EGS comprises a ten to fifteen nucleotide sequence complementary to AD7c-NTP mRNA (corresponding to the miss-sequenced regions) and a 3'-NCCA nucleotide sequence, wherein N is preferably a purine (Id.). After NTP EGS molecules are delivered to cells, as described below, the molecules bind to the targeted NTP mRNA species by forming base pairs between the NTP mRNA and the complementary NTP EGS sequences, thus promoting cleavage of NTP mRNA by RNase P at the nucleotide at the 5' side of the base-paired region (Id.).

Examples of such external guide sequences are:

```
CAC TGC ACT TNC CA       (Seq. ID No. 12)

CCA GGT GTA GNC CA       (Seq. ID No. 13)

CAA GGT CCA GNC CA       (Seq. ID No. 14)
```

Included as well in the present invention are pharmaceutical compositions comprising an effective amount of at least one NTP antisense oligonucleotide, triple helix-forming oligonucleotide, NTP ribozyme or NTP EGS of the invention in combination with a pharmaceutically acceptable carrier. Preferably, the NTP antisense oligonucleotide, triple helix-forming oligonucleotide, NTP ribozyme or NTP EGS is coadministered with an agent which enhances the uptake of the NTP antisense oligonucleotide, triple helix-forming oligonucleotide, ribozyme or NTP EGS molecule by the cells. For example, the NTP antisense oligonucleotide, triple helix-forming oligonucleotide, NTP ribozyme or NTP EGS may be combined with a lipophilic cationic compound which may be in the form of liposomes, as described above. Alternatively, the NTP antisense oligonucleotide, NTP triple helix-forming oligonucleotide, NTP ribozyme or NTP EGS may be combined with a lipophilic carrier such as any one of a number of sterols including cholesterol, cholate and deoxycholic acid. A preferred sterol is cholesterol.

The NTP antisense oligonucleotide, NTP triple helix-forming oligonucleotide, NTP ribozyme or NTP EGS, and the pharmaceutical compositions of the present invention may be administered by any means that achieve their intended purpose. For example, administration may be by parenteral, subcutaneous, intravenous, intramuscular, intraperitoneal, transdermal, intrathecal or intracranial routes. The dosage administered will be dependent upon the age, health, and weight of the recipient, kind of concurrent treatment, if any, frequency of treatment, and the nature of the effect desired. For example, as much as 700 milligrams of antisense oligodeoxynucleotide has been administered intravenously to a patient over a course of 10 days (i.e., 0.05 mg/kg/hour) without signs of toxicity (Sterling, "Systemic Antisense Treatment reported," *Genetic Engineering News* 12(12):1, 28 (1992)).

Compositions within the scope of this invention include all compositions wherein the NTP antisense oligonucleotide, NTP triple helix-forming oligonucleotide, NTP ribozyme or NTP EGS is contained in an amount which is effective to achieve inhibition of proliferation and/or stimulate differentiation of the subject cancer cells, or alleviate AD. While individual needs vary, determination of optimal ranges of effective amounts of each component is with the skill of the art.

In addition to administering the NTP antisense oligonucleotides, triple helix-forming oligonucleotides, ribozymes, or NTP EGS as a raw chemical in solution, the therapeutic molecules may be administered as part of a pharmaceutical preparation containing suitable pharmaceutically acceptable carriers comprising excipients and auxiliaries which facilitate processing of the NTP antisense oligonucleotide, triple helix-forming oligonucleotide, ribozyme, or NTP EGS into preparations which can be used pharmaceutically. Suitable formulations for parenteral administration include aqueous solutions of the NTP antisense oligonucleotides, NTP triple helix-forming oligonucleotides, NTP ribozymes, NTP EGS in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

Alternatively, NTP antisense oligonucleotides, NTP triple helix-forming oligonucleotides, NTP ribozymes, and NTP EGS can be coded by DNA constructs which are administered in the form of virions, which are preferably incapable of replicating in vivo (see, for example, Taylor, WO 92/06693). For example, such DNA constructs may be administered using herpes-based viruses (Gage et al., U.S. Pat. No. 5,082,670). Alternatively, NTP antisense oligonucleotides, NTP triple helix-forming oligonucleotides, NTP ribozymes, and NTP EGS can be coded by RNA constructs which are administered in the form of virions, such as retroviruses. The preparation of retroviral vectors is well known in the art (see, for example, Brown et al., "Retroviral Vectors," in *DNA Cloning: A Practical Approach*, Volume 3, IRL Press, Washington, D.C. (1987)).

According to the present invention, gene therapy can be used to alleviate AD by inhibiting the inappropriate expression of a particular form of NTP. Moreover, gene therapy can be used to alleviate AD by providing the appropriate expression level of a particular form of NTP. In this case, particular NTP nucleic acid sequences may be coded by DNA or RNA constructs which are administered in the form of viruses, as described above. Alternatively, "donor cells" may be modified in vitro using viral or retroviral vectors containing NTP sequences, or using other well known techniques of introducing foreign DNA into cells (see, for example, Sambrook et al., supra). Such donor cells include fibroblast cells, neuronal cells, glial cells, and connective tissue cells (Gage et al., supra). Following genetic manipulation, the donor cells are grafted into the central nervous system and thus, the genetically-modified cells provide the therapeutic form of NTP (Id.).

Moreover, such virions may be introduced into the blood stream for delivery to the brain. This is accomplished through the osmotic disruption of the blood brain barrier prior to administration of the virions (see, for example, Neuwelt, U.S. Pat. No. 4,866,042). The blood brain barrier may be disrupted by administration of a pharmaceutically effective, nontoxic hypertonic solution, such as mannitol, arabinose, or glycerol (Id.).

Having now generally described the invention, the same will be more readily understood through reference to the following Examples which are provided by way of illustration, and are not intended to be limiting of the present invention, unless specified.

EXAMPLES

Example 1

Isolation of the AD7c-NTP cDNA

A cDNA library was prepared commercially (Invitrogen Corp., San Diego, Calif.) using RNA extracted from the temporal lobe of an individual with end-stage AD. The library was ligated into the pcDNA2 vector (In Vitrogen). To isolate the AD7c-NTP gene, approximately $5 \times 10^5$ transformed and IPTG induced (Sambrook, J. et al. "Molecular Cloning, A Laboratory Manual," Cold Spring Harbor Laboratory Press, Cold Spring Harbor, N.Y.) *E. coli* colonies were screened using polyclonal antibodies to human PTP (Gross, J. et al., "Isolation, Characterization, and Distribution of an Unusual Pancreatic Human Secretory Protein," *J. Clin. Invest.* 76:2115–2126 (1985)), followed by radiolabeled anti-human IgG (Amersham, Arlington Heights, Ill.) (Sambrook, J. et al. (1989); and Ausubel, F. M. et al., "Current Protocols in Molecular Biology," New York, N.Y., John Wiley & Sons (1988)). Restriction endonuclease fragments (XhoI-PstI; PstI-PvuII; PvuII-HindIII) of AD7c-NTP were subcloned into pGem7 (Promega Corp., Madison, Wis.), and the nucleotide sequence of both strands was determined by the dideoxy chain termination method using T7 DNA polymerase (Ausubel, F. M. et al. (1988)). Additional gene specific primers were generated to generate sequences that overlapped the fragments. The DNA sequence was assembled with the MacVector Software version 4.5 and analyzed using a Sequence Analysis Software of the Genetics Computer Group version 7.3 as implemented on a MicroVax II computer. Database searches were performed using the BLAST network service of the National Center for Biotechnology Information.

Characteristics of the AD7c-NTP CDNA Isolated from an AD Brain Library

The AD7c-NTP cDNA contains 1442 nucleotides and begins with an oligo-dT track. The nucleotide sequence contains an 1125-nucleotide open reading frame starting with the first AUG codon, and a 302-nucleotide untranslated sequence that contains an AATAAA polyadenylation signal (FIG. 1). Bestfit and GAP analysis revealed the presence of four Alu-type sequences embedded in the open reading frame (nucleotides 1–170, 423–593, 595–765, and 898–1068), and a near-duplication (85% identical) of the first 450 nucleotides starting at nucleotide 898. BLAST database comparisons disclosed 3 regions of significance (67–89%) homology to the Huntington's disease region, chromosome 4p16.3 (Gusella, J. F. et al., "A Polymorphic DNA Marker Genetically Linked to Huntington's Disease," *Nature* 306:24–238 (1983)) (FIG. 1), but no alignment with the IT15 Huntington cDNA which contains longer than normal $(CAG)_n$ repeats in individuals with Huntington's disease (The Huntington's Disease Collaborative Research Group, "A Novel Gene Containing a Trinucleotide Repeat that is Expanded and Unstable on Huntington's Disease Chromosomes," *Cell* 72:971–983 (1993)).

The translated 375 amino acid sequence has a predicted molecular weight of 41,718 and estimated pI of 9.89, and is rich in Ser (11.7%) and Pro (8.8%) residues. Kyte-Doolittle and Chou-Fasman hydrophilicity and Hopp-Woods surface probability profiles predict a 15 amino acid hydrophobic leader sequence, and 7 membrane-spanning regions. Corresponding with the organization of the cDNA, subsequent analysis of the protein revealed four 83% to 91%, identical repeated (once or twice) antigenic domains between 9 and 23 amino acids in length (FIG. 1). Protein subsequent analysis demonstrated 21 cAMP, calmodulin-dependent protein kinase II, protein kinase C, or glycogen synthase kinase 3 phosphorylation sites, and one myristyration site. In addition, a single tgf motif (Residues #4414 #53) was detected. Comparison of the AD7c-NTP amino acid sequence with the genebank database revealed four regions of significant homology to the β-subunit of integrin (72%–80%), the alternatively spliced A4 form of the neurofibromatosis 2 gene (72%–81%), myelin oligodendroglial glycoprotein- 16 precursor protein (70%–76%), human integral membrane protein (55%–85%), and human decay accelerating factor 2 precursor (62%–68%), and two regions with homology to the c-rel protooncogene transforming protein (Residues 56–84: 65%; Residues 287–295: 88%) (FIG. 1). Residues 5–24 are 75% identical to a region of the IGF1/insulin receptor hybrid, and residues 4–24, 47–79, 109–132, 227–261, and 227–360 exhibit 57% to 76% identity with the human transformation-related protein. In addition, two serine/threonine kinase protein domains (Residues 6–48, and 272–294) were identified.

The in vitro translated protein and pTrcHis-AD7c-NTP recombinant protein purified by metal chelate chromatography and cleaved from the fusion partner had molecular masses of ~39–42 kD by SDS-PAGE or Western blot analysis (FIG. 2). In addition, in Bosc cells transfected with the AD7c-ITP cDNA ligated into the pcDNA3 vector (Invitrogen, San Diego, Calif.), a single ~39–42 kD protein was detected by Western blot analysis using the N3I4 monoclonal antibody. In two-site immunoradiometric assays and immunoblotting studies, the AD7c-NTP recombinant protein exhibited specific immunoreactive binding with all of the polyclonal and monoclonal antibodies generated with purified pTrcHis-AD7c-NTP recombinant protein. No immunoreactivity with AD7c-NTP was detected using pre-immune rabbit sera, non-relevant rabbit polyclonal antibodies to GAP-43, or non-relevant monoclonal antibodies to Dengue virus or FB50 (FIG. 2).

Example 2

In Vitro Expression of AD7c-NTP

Antisense and sense cRNAs were transcribed from AD7c-NTP cDNA plasmid with KpnI and XhoI, respectively. The cRNA transcripts were translated in a rabbit reticulocyte lysate system (Stratagene, La Jolla, Calif.) in the presence of [$^{35}$S]methionine (Dupont-New England Nuclear, Boston, Mass. ), and the products of in vitro translation were analyzed by SDS-PAGE and autoradiography. The AD7c-NTP cDNA was ligated into the pTrcHis expression vector (Invitrogen Corp., San Diego, Calif.) which encodes a 5 N 6-His Tag sequence used to isolate the fusion protein by metal chelate chromatography. Recombinant fusion protein induction in transformed E. coli was achieved by the addition of 1 mM IPTG during log phase growth. The fusion protein was affinity purified (Ausubel, F. M. et al. (1988)) using ProBond resin (Invitrogen Corp., San Diego, Calif.), and detected by Western blot analysis (Harlow, E. and Lane, D., "Antibodies: A Laboratory Manual," Cold Spring Harbor Laboratory, Cold Spring Harbor, N.Y. (1988)) with antibodies to do T7-tag fusion partner (Novogen). The tag was then cleaved with entrokinase to give the AD7c-NTP protein. (Ausubel, R. M et al. (eds.) in Current Protocols in Molecular Biology, John Wiley & Sons, Inc., New York, N.Y., 1994.

Example 3

Generation of Polyclonal and Monoclonal Antibodies to Recombinant AD7c-NTP

Polyclonal antibodies were generated in rabbits immunized with affinity purified recombinant AD7c-NTP protein. Monoclonal antibodies were generated in Balb/c mice immunized intraperitoneally with 50 μg of purified recombinant AD7c-NTP protein emulsified in complete Freund's adjuvant (Harlow, E. and Lane, D. (1988); and Wands, J. R. and Zurawski, V. R., Jr., "High Affinity Monoclonal Antibodies to Hepatitis B surface Antigen (HBsAg) produced by Somatic Cell Hybrids," *Gastroeneology* 80I:225–232 (1981)). The mice were boosted 6 to 10 weeks later, with 10 μg AD7c-NTP by tail vein injection. Spleenocytes were fused with SP-0 myeloma cells (Harlow, E. and Lane, D. (1988) and Wands, J. R. and Zurawski, V. R., Jr. (1981)). The cells were grown in HAT medium, and hybridomas producing anti-AD7c-NTP antibody were identified by solid phase immunoassay (Bellet, D. H. et al., "Sensitive and Specific Assay for Human Chorionic Gonadotropin Based on Anti-Peptide and Anti-Glycoprotein Monoclonal Antibodies: Construction and Clinical Implications," *J. Clin. Endocrinol. Metabol.* 63:1319–1327(1988)). The binding specificity of the immunoglobulin fractions of polyclonal immune sera and the hybridomasupernatants was confirmed by radioimmunoassay (RIA) and Western blot analysis with recombinant AD7c-NTP, and by Western blot analysis and immunohistochemical staining of AD and aged control brains. In a panel of 25 hybridomas, 3 MoAbs exhibited similar levels of immunoreactivity with purified native PTP and recombinant AD7c-NTP, and therefore were further characterized (Table 1).

TABLE 1

Profiles of Immunoreactivity Exhibited by AD7c-NTP Monoclonal Antibodies

| Antibody | Western Blot | ICC* | AD Specific** | Distribution of Labeling in AD Brains |
| --- | --- | --- | --- | --- |
| N2B10 | Y: Reducing | Negative | N/A | None |
| N2I5 | Y: Reducing | Negative | N/A | None |
| N2J1 | Yes | ++ | Yes | Neuropil threads, irregular neurites, axons |
| N2R1 | No | Negative | N/A | None |
| N2S6 | Y: Reducing | ++++ | Yes | Neurons |
| N2T8 | Y: Reducing | ++++ | Yes | Degenerating neurons, NFT, irregular neurites |
| N2U6 | Yes | +++ | Yes | Neuropil threads, NFT |

TABLE 1-continued

Profiles of Immunoreactivity Exhibited by AD7c-NTP Monoclonal Antibodies

| Antibody | Western Blot | ICC* | AD Specific** | Distribution of Labeling in AD Brains |
|---|---|---|---|---|
| N3A13 | No | + | No | None |
| N3C11 | No | ++ | No | None |
| N3D12 | No | + | No | None |
| N3I4 | Y: Nonreducing | Negative | N/A | None |
| N2-36 | No | + | Yes | NFT, Swollen neurites |
| N2-22-11 | No | Negative | N/A | None |
| Polyclonal | Yes | ++++ | Yes† | Degenerating neurons, irregular neurites |

*ICC = Immunocytochemistry; NFT = neurofibrillary tangles
**AD-specific: Immunoreactivity only detected in histologically normal neutrons and fibers in AD tissue sections (N2S6), or in degenerating neuronal cell bodies and processes detected in AD.
†= following formic acid treatment only.

Profiles of AD7c-NTP Immunoreactivity Revealed with MoAbs (Table 1): The findings summarized below are representative of the observations made in 6 end-stage AD and 5 aged control brains. Twenty-five of the AD7c-NTP MoAbs were characterized by immunocytochemical staining. Table 1 details features of 13 AD7c-NTP MoAbs. The other 12 MoAbs were excluded from the list because either they were not suitable for immunocytochemical staining and Western immunoblot studies due to low-level binding (N=9), or they exhibited cross-immunoreactivity with pancreatic thread protein (N=3). Among the 13 AD7c-NTP MoAbs that were further characterized, only 8 exhibited immunoreactivity in neuronal perikarya, neuropil fibers, white matter fibers (axons), or AD neurodegenerative lesions. The other 5 were non-immunoreactive in histologic sections.

In Table 1, AD-specific binding refers to the detection of degenerating neurons, neurofibrillary tangles, irregular swollen neurites and axons, or immunoreactivity in histologically intact neurons in AD but not control brains. Four AD7c-NTP MoAbs (N2–36, N3-C11, N2S6, N2-T8) exhibited intense degrees of immunocytochemical staining in cortical neurons, particularly pyramidal cells in layers 3 and 5. Two MoAbs (N2-U6, N2-S6) prominently labeled neuropil and white matter fibers (axons), and 5 (N2-U6, N3-C11, N2-S6, N2-T8, N2-J1) detected A2B5+ and GFAP+ protoplasmic (Type 2) astrocytes in the cerebral cortex and white matter. Two AD7c-NTP MoAbs (N2-U6 and N2-T8) exhibited intense labeling of cortical neurons and swollen, irregular (dystrophic) neuropil neurites in AD, but low-level or absent labeling in aged control brains. Most striking was the immunoreactivity observed in AD-associated neurodegenerative lesions using the N2–36, N2-T8, N2-U6 MoAbs. N2-T8 detected intracellular neurofibrillary tangles as well as degenerated neurons without neurofibrillary tangles; N3-D12, N2-T8, and N2-J1 labeled swollen dystrophic axons and fine neuritic processes, particularly in superficial layers of the cerebral cortex; and N2-U6 and N2-J1 labeled wavy irregular threadlike structures detected only in AD brains. N2J1 very prominently labeled irregular threadlike structures, dystrophic neurites, and swollen axons, but exhibited minimal labeling of neurons perikarya or glial cells. The negative control 5C3 MoAb to Hepatitis B virus was not immunoreactive with adjacent sections of the same brains.

In the Examples which follow, polyclonal and the N3I4, N2J1, and N2U6 monoclonal AD7c-NTP antibodies were employed.

Example 4

Human Brain Tissue

Human brain tissue was obtained from the Alzheimer's Disease Research Center brain bank at the Massachusetts General Hospital (MGH-ADRC). All brains were harvested within 12 hr of death, and the histopathological diagnosis of AD was rendered using CERAD criteria (Mirra, S. S. et al., "The Consortium to Establish a Registry for Alzheimer's Disease (CERAD). II. Standardization of the Neuropathological assessment of Alzheimer's Disease," Neurology 41:479–486 (1991)). The AD group (N=17) had a mean age of 76.3±8.8 years, a mean brain weight of 1117±101 grams, and a mean postmortem interval of 7.3±3.9 hours. The control group (N=11) had a mean age of 78.0±6.2 years, a mean brain weight of 1274±115 grams, and a mean postmortem interval of 8.3±3.6 hours. In addition, 4 cases of early probable AD with cognitive decline and moderate AD histopathological lesions, and 2 cases of diffuse Lewy body disease (Kosaka, K. "Dementia and Neuropathology in Lewy Body Disease," Adv. Neurol. 60:456–463 (1993)) (DLBD: an AD-related CNS neurodegenerative disease) were studied. Fresh frozen frontal and temporal lobe tissue was used for Northern and Western blot analyses. Postmortem cerebrospinal fluid (CSF) samples (8 AD; 7 control; 2 DLBD) were used to detect AD7c-NTP by Western blot analysis. Paraffin-embedded histological sections were used to localize AD7c-NTP gene expression by in situ hybridization and immunohistochemical staining.

Example 5

Northern Analysis of AD7c-NTP mRNA Expression

Samples (15 μg) of total RNA isolated (Ausubel, F. M. et al. (1988)) from AD and aged control frontal lobe tissue (Brodmann Area 11), and normal adult human kidney, liver, spleen, gastrointestinal tract, ovaries, fallopian tubes, uterus, thyroid, lung, skeletal muscle, and pancreas, were subjected to Northern hybridization analysis using $2 \times 10^6$ dpm/ml of $[\alpha^{32}P]$dCTP-labeled AD7c-NTP cDNA probe (specific activity $\|10^8$ dpm/μg DNA) generated by the random hexamer method (Ausubel, F. M. et al. (1988)). The blots were subsequently washed in stepwise dilutions of 5×SSC (1×SSC is 0.15 M NaCl plus 0.015 M sodium citrate) containing 0.5% SDS (Sambrook, J. et al. (1989); Ausubel, F. M. et al. (1988)), and finally in 0.1×SSC/0.5% SDS at 65° C. To evaluate RNA loading, the blots were stripped of probe and re-hybridized with a 10-fold molar excess of a $[\gamma^{32}P]$ATP-labeled synthetic 30mer corresponding to 18s ribosomal RNA (de la Monte, S. M. and Bloch, K. D. (1996)). The results were analyzed by autoradiography and densitometry (ImageQuant, Molecular Dynamics, Inc).

Results: AD 7c-NTP mRNA Expression in AD and Aged Control Brains

In Northern blot hybridization studies, AD7c-NTP cDNA probes detected 1.4 kB and 0.9 kB mRNA transcripts in adult human frontal and temporal lobe tissue, but not pancreas, kidney, liver, spleen, gastrointestinal tract (various regions) ovaries, fallopian tubes, uterus, thyroid, lung, skeletal muscle, testis, and thymus were negative. Both 1.4 kB and 0.9 kB AD7c-NTP mRNA transcripts were detected in AD and aged control brains, but the levels of expression were increased in AD. With values normalized to 18S RNA signals to correct for differences in loading and non-specific degradation, densitometric analysis of non-saturated autoradiograms revealed significantly higher mean levels of both the 1.4 kB ($P<0.01$) and the 0.9 kB ($P<0.05$) AD7c-NTP transcripts in AD compared with normal aged control brains.

Example 6

Reverse Transcriptase-polymerase Chain Reaction Amplifcation (RT-PCR) Studies

Samples of total RNA (2 μg) isolated from human brain, PNET1 and PNET2 human CNS neuronal cell lines (The, I. et al., "Neurofibromatosis type 1 Gene Mutations in Neuroblastoma," *Nature Genet.* 3:62–66 (1993)) (positive controls), SH-Sy5y human neuroblastoma cells (Biedler, J. et al., "Morphology and Growth, Tumorigenicity, and Cytogenetics of Human Neuroblastoma Cells in Continuous Culture," *Cancer Res.* 33:2643–2652 (1973)), and human pancreas and liver (negative controls) were reverse transcribed using random hexamer primers (Ausubel, F. M. (1988)) and Superscript™ reverse transcriptase (Gibco-BRL, Grand Island, N.Y.). The cDNA products (10%) were subjected to PCR amplification to detect AD7c-NTP sequences using the primers: (459–480) 5' TGTCCCACTCTTACCCAGGATG [Seq ID No. 5] and (849–826) 5' AAGCAGGCAGATCA-CAAGGTCCAG [Seq. ID No. 6]. β-actin control primers (Dallman, M. J. and Porter, A. C. G., "Semi-Quantitative PCR for the Analysis of Gene Expression," In: *PCR A Practical Approach*, M. J. McPherson et al. (eds.), IRL Oxford University Press, Oxford, pp. 215–224 (1991)) (5' AATGGATGACGATATCGCTG Seq. ID No. 7; 5'-ATGAG-GTAGTCTGTCAGGT,[Seq. ID No. 8]) were incorporated into all studies. Each cycle of PCR amplification consisted of denaturation at 95 ° C. for 30 secs, annealing at 60° C. for 30 secs, and extension at 72° C. for 1 min. After 30 cycles and a final 10 minute extension at 72 ° C., approximately 10 percent of the PCR products were analyzed by agarose gel electrophoresis and Southern hybridization using a [$\gamma^{32}P$] dATP-labeled oligonucleotide probe corresponding to nucleotides 702–720 of the AD7c-NTP cDNA. The remaining PCR products were electrophoretically fractionated and ligated into PCRII TA cloning vectors (InVitrogen Corp, San Diego, Calif.). The nucleotide sequences of clones isolated from 6 brain samples were determined by the dideoxy chain termination method (Sambrook, J. et al., (1989); Ausubel, F. M. (1988)).

Expression of AD7c-NTP mRNA in human brain was verified by RT-PCR amplification of RNA isolated from 6 AD and 5 aged control brains (frontal lobe). The expected 390 nucleotide PCR product was obtained with all samples. The specificity of the PCR products was demonstrated by Southern blot analysis using [$^{32}P$]-labeled oligonucleotide probes corresponding to internal sequences, and by determining that the nucleic acid sequences of the 390-nucleotide PCR products cloned from 5 AD brains were identical to the sequence underlined in FIG. 1. In the RT-PCR amplification studies, AD7c-NTP PCR products were also detected using RNA isolated from PNET1, PNET2 and SH-Sy5y neuronal cells, but not human pancreas or liver. All samples analyzed yielded positive RT-PCR products using the β-actin primers.

Example 7

In Situ Hybridization

Paraffin sections (10 μm thick) of AD and control brains were hybridized with antisense and sense (negative control) AD7c-NTP cRNA probes (de la Monte S. M. et al., (1995); de la Monte, S. M. and Bloch, K. D. (1996)) generated from cDNA templates linearized with KpnI or XhoI, and labeled with [11-digoxigenin]UTP using SP6 to T7 DNA dependent RNA polymerase (Melton, D. A. et al. "Efficient in Vitro Synthesis of Biologically Active RNA and RNA Hybridization Probes from Plasmids Containing a Bacteriophage SP6 Promoter," *Nucl. Acids Res.* 12:7035–7056 (1984)). Specifically bound probe was detected with alkaline phosphatase-conjugated sheep F(ab')$_2$ anti-digoxigenin (Boehringer-Mannheim Inc.) and X-phosphate/5-bromo-4-chloro-3-indolyl-phosphate/nitro-blue-tetrazolium-chloride (de la Monte, S. M. and Bloch, K. D. (1996)). The probe specificity was confirmed by Northern blot analysis of brain using identical CRNA probes labeled with [$\alpha^{32}P$]UTP.

Results: Cellular Localization of AD7c-NTP mRNA in Human Brain

In situ hybridization studies using [11-digoxigenin]UTP-labeled antisense cRNA probes demonstrated AD7c-NTP-related mRNA transcripts in frontal (Brodmann Area 11) and temporal (Brodmann Area 21) cortex neurons in both AD (N=6) and aged control (N=4) brains (FIG. 3). However, darkfield microscopy revealed strikingly elevated levels of AD7c-NTP mRNA expression in both temporal and frontal cortex neurons in AD relative to aged control brains, corresponding with the results of Northern blot analysis. Low levels of AD7c-NTP mRNA transcripts were also detected in cortical and white matter glial cells in AD. AD7c-NTP mRNA transcripts were not detected in cerebral blood vessels, and specific hybridization signals were not observed in any of the specimens hybridized with digoxigenin-labeled sense strand cRNA probes.

Example 7

Immunodetection of AD7c-NTPR Expression

Western immunoblotting studies (Harlow, E. and Lane, D. (1988)) were performed using protein extracts (60 μg samples) generated from postmortem frontal and temporal lobe tissue, and various non-CNS tissues homogenized in RIPA buffer (Ausubel, F. M. et al. (1988)). In addition, 40 μl samples of postmortem or antemortem cerebrospinal fluid were evaluated by Western blot analysis. The blots were probed with rabbit polyclonal (1:800) or N3I4, N2U6, or N2J1 mouse monoclonal (5 μg/ml) anti-AD7c-NTP. Antibody binding was detected with horseradish peroxidase-conjugated secondary antibody diluted 1:25,000 (Pierce), and Supersignal enhanced chemiluminescence reagents (Pierce). The levels of AD7c-NTP expression were quantified by volume densitometric scanning of the autoradiograms (ImageQuant; Molecular Dynamics Inc., Sunnyvale, Calif.). Cellular localization of AD7c-NTP immunoreactivity was demonstrated in paraffin-embedded histological sections of frontal (Brodmann Area 11) and temporal (Brodmann Area 21) lobe from AD and age-matched control brains. The sections were immunostained by the avidin-biotin horseradish peroxidase complex method (de la Monte, S. M. et al. (1995); and de la Monte, S. M. and Bloch, K. D. (1996)) using the N2J1 and N2U6 AD7c-NTP monoclonal antibodies. Adjacent sections were immunostained with monoclonal antibodies to glial fibrillary acidic protein as a positive control, and with monoclonal antibodies to Dengue virus as a negative control.

Results: Characterization of AD7c-NTP Antibody Binding by Western Blot Analysis

In Western immunoblotting studies of protein extracted from human frontal and temporal lobe tissue, broad ~39–45 kD bands of AD7c-NTP immunoreactivity were detected with the polyclonal and 11 of the 25 monoclonal antibodies. When the proteins were electrophoretically fractionated in 15% Laemmli gels and probed with the N3I4, N2U6, or N2J1 monoclonal antibodies, the ~39–45 kD AD7c-NTP-immunoreactive molecules were resolved into 3 or 4 tightly clustered bands (FIG. 2E), possibly representing different degrees of AD7c-NTP phosphorylation. In addition, the polyclonal and 4 of the monoclonal antibodies detected 18–21 kD AD7c-NTP-immunoreactive proteins in brain (FIG. 2E). Western blot analysis of non-CNS tissues revealed no specific binding with the AD7c-NTP antibodies.

Example 8

In vitro Expression Studies

The AD7c-NTP cDNA was ligated into the pcDNA3 mammalian expression vector which contains a CMV promoter (InVitrogen, San Diego, Calif.). SH-Sy5y cells were transfected with either pcDNA3-AD7c-NTP or pcDNA3 (empty vector, negative control), and selected with G418. Stably transfected cell lines were examiner for growth properties, morphology, and expression of AD7c-NTP. Cell growth was assessed by measuring [$^3$H] thymidine incorporation into DNA and determining the density of viable cells in the cultures. Cells grown in chamberslides were immunostained using N3I4 monoclonal antibody. AD7c-NTP expression was also evaluated by Western blot analysis with the N3I4 antibody.

Results: Over-Expression of AD7c-NTP in Neuronal Cells Leads to Apoptosis, Neuritic Sprouting Which are Characteristic of Alzheimer's Disease Over-expression of AD7c-NTP in SH-Sy5y neuronal cells stably transfected with pcDNA3-AD7c-NTP resulted in significantly lower densities of viable cells in the cultures, despite normal or elevated levels of DNA synthesis (FIG. 5). This result was reproducible in other neuronal cells lines and using other expression vectors. Reduced cell density in the cultures was caused by increased cell death. The attendant increase in nuclear p53 expression in AD7c-NTP transfected cells suggests that the cell death is likely to be mediated by apoptosis. Subconfluent cultures of SH-Sy5y cells transfected with pcDNA3 contained round or spindled shaped cells with few or no processes (FIG. 6A). In contrast, SH-Sy5y cells transfected with pcDNA3-AD7c-NTP exhibited extensive neuritic growth with fine interconnecting processes detected on most cells (FIGS. 6B–6D). In addition, pcDNA3-AD7c-NTP transfected cultures always contained numerous round, refractile floating cells (dead) which failed to exclude Trypan blue dye. Immunocytochemical staining of stationary cultures using the N3I4 monoclonal antibody revealed intense labeling of the cell bodies and cell processes of SH-Sy5y cells transfected with pcDNA3-AD7c-NTP (FIGS. 6F and 6G), and absent immunoreactivity in SH-Sy5y cells transfected with pcDNA3 (empty vector) (FIG. 6E). These studies demonstrate that over expression of AD7c-NTP in transfected neuronal cells promotes neuritic sprouting and cell death, two of the major features of Alzheimer's disease neurodegeneration. Thus, transfected cell lines and transgenic animals which overexpress the AD7c-NTP will be useful for screening drugs that might be effective in reducing AD7c-NTP expression and, thereby, treating or preventing the onset of Alzheimer's disease.

Example 9

AD 7c-NTP Protein Expression in AD and Aged Control Brains

Western blot analysis and immunohistochemical staining of AD and aged control brains were performed using the N3I4, N2U6, and N2J1 monoclonal AD7c-NTP antibodies. In AD and aged control brains, ~39–45 kD proteins were detected with all 3 monoclonal antibodies. In addition, ~18–21 kD proteins were detected with the N2U6 and N2J1 antibodies. Densitometric analysis of the autoradiograms demonstrated significantly higher levels of the ~39–45 kD AD7c-NTP in AD relative to aged control frontal lobe tissue (FIG. 2D). In addition, expression of the ~18–21 kD AD7c-NTP-immunoreactive proteins was also increased in AD, but studies have not yet determined whether these molecules represent cleavage products of the ~39–45 kD AD7c-NTP, or a unique protein encoded by another cDNA. In a small series, comparisons between early and late AD revealed higher levels of AD7c-NTP immunoreactivity in brains with end-stage disease (FIG. 2E). Using the N3I4 antibody, Western blot analysis detected the presence of ~39–45 kD AD7c-NTP molecules in postmortem CSF, and higher levels in AD relative to aged control samples (FIG. 2F). Immunohistochemical staining studies with polyclonal and several brain-specific monoclonal antibodies localized AD7c-NTP immunoreactivity in neurons, neuropil fibers, and white matter fibers in AD and control brains. In immunohistochemical staining studies, the N2U6 and N2J1 antibodies exhibited intense immunoreactivity in intact as well as degenerating cortical neurons and dystrophic neurites in AD brains, but low-level or absent immunoreactivity in aged control brains (FIG. 4). Omission or pre-adsorption of the primary antibody with recombinant AD7c-NTP protein, or the application of non-relevant primary antibody (negative controls) also yielded negative immunostaining results. All sections of brain exhibited positive immunoreactivity with monoclonal antibodies to glial fibrillary acidic protein (positive control).

These studies demonstrate elevated levels of AD7c-NTP expression in AD relative to aged control brains, and abnormal AD7c-NTP gene expression localized in AD brain neurons by in situ hybridization and immunohistochemical staining. Although two distinct mRNA transcripts and at least two distinct protein species were detected in brain, the levels of the mRNA and protein corresponding to AD7c-NTP were increased in AD. We have not yet determined whether the smaller transcripts and protein species are distinct, or represent alternately spliced forms of a single gene. Although the cDNA was isolated from a library prepared with RNA isolated from a single AD brain, the RT-PCR studies confirmed the presence of identical sequences in 6 different AD brains. Since the AD7c-NTP cDNA exhibits no significant primary sequence homology with the human pancreatic protein (Watanabe, T. et al., "Complete Nucleotide Repeat that is expanded and Unstable on Huntington's Disease Chromosomes," *Cell* 72:971–983 (1993)), the cross-reactivity of polyclonal antibodies with AD7c-NIP molecule probably occurs through conformational epitopes. Increased expression of AD7c-NTP was observed in both histologically intact and degenerating neurons and cell processes, and a recent study suggested that AD7c-NTP protein expression occurs early in AD neurodegeneration.

Example 10

In Vitro Drug Screening System

AD7c-NTP was cloned into a Lac-Switch expression vector (Stratgene), and CYZ neuronal cells were stably transformed with the construct. Several cell lines were selected that expressed AD7c-NTP at various levels, Lac A-Lac F, after induction of protein expression with IPTG. Experiments were done to determine the effect (e.g., change in morphology, gene expression, viability, etc.) of AD7c-NTP expression on neuronal cells, thereby generating markers useful for screening, in vitro, potential pharmacologic agents for the treatment of AD.

Expression levels were determined by Microtiter Immunocytochemical Elisa Assay (MICE). Briefly, $10^4$ cells/well were seeded into 96-well plates, and were induced to express AD7c-NTP for a period of 6–18 hrs; additionally, in some experiments, cells were exposed to toxins or protective agents for a similar period of time. At the end the treatment period, cells were fixed, permeabilized and immunostained with the appropriate antibody following the ABS procedure. Quantitation was done by incubating cells with a soluble chromagen, stopping the reaction with 2M $H_2SO_4$ and determining chromagen absorbance in an automated ELISA reading machine. After staining with Coommassie Blue, the ratio of immunoreactivity (i.e. bound chromagen) to Coommassie Blue absorbance was determined (MICE units), and the results were graphed. Alternatively, immunoreactivity may also be determined with a precipitating chromagen (e.g. DAB, TruBlue or AEC).

For Experiments determining cell viability, after culture and treatment as for the MICE assay, culture media was replaced with a Crystal Violet/PBS/formalin solution. After staining, cells were rinsed thoroughly and lysed with a PBS/1% SDS solution, and absorbance was determined with an automated ELSA reader. Results were graphed as percent viability.

Results: Over-Expression of AD7c-NTP in Neuronal Cells Leads to Alterations in Gene Expression, Cell Viability and Toxin Hypersensitivity Expression of AD7c-NTP results in altered expression of genes associated with AD (Tau, bA4 amyloid), neuritic sprouting (synaptophysin) and apoptosis (p53, SC95-Fas, NO-Tyr, NOS3) (FIGS. 7A–7C and 8A–8D). In FIGS. 7A–7C, the percent change in expression, 24 hrs. after AD7c-NTP induction, is presented for the indicated genes. In the absence of AD7c-NTP expression (FIG. 7A), little or no change in gene expression is observed in Lac A-control, nonexpressing cells; however, similar experiments done with Lac B (FIG. 7B) and Lac F (FIG. 7C) cells induced to express different levels of AD7c-NTP (B6) demonstrate marked changes in gene expression. For example, NOS3 is expressed at almost twice the normal level in the Lac B-B6 experiment (FIG. 7B) than in Lac A-control cells (FIG. 7A).

FIGS. 8A–8D demonstrate that altered gene expression is dependent on the level of AD7c-NTP induction. Results are presented for the NTP (FIG. 8A), Synaptohysin (FIG. 8B), Tau (FIG. 8C) and p53 (FIG. 8D) genes as percent change in expression as a function of IPTG induction of AD7c-NTP expression in stably transfected, CYZ neuronal cells. LacB (filled square) and LacF (open circle) cells were exposed to the indicated amounts of IPTG (1–5 mM) for 24 hrs. These data indicate that increased concentrations of IPTG leads to an up-regulation of all genes examined.

Two assays were used to evaluate the effects of AD7c-NTP expression in CYZ neuronal cells: metabolic activity was measured by the MTT assay (FIG. 9A), and cell death was measured by the CV viability assay (FIG. 9B). Results are expressed as percent change in MTT activity or cell viability 24 hrs. after IPTG induction relative to untreated, parallel control cultures. Six different clones, LacA-LacF, were assayed after IPTG induction (B6) and compared to LacA control cells lacking AD7c-NTP. For all 6 clones examined, stimulation of AD7c-NTP expression results in substantially reduced metabolic activity relative to control cells (FIG. 9A). Cell death was induced in LacB-B6 and LacF cells, and reduced cell viability was observed in LacA-B6 and LacE-B6 clones.

Decreased cell viability of cells expressing AD7c-NTP is exacerbated by oxidative stress. When LacB and LacF cells were induced with 3mM IPTG (B6) for 24 hrs or 48 hrs. and exposed to toxins that increase oxidative stress for 6 hrs or 24 hrs. (FIGS. 10A and 10B, respectively), cell viability decreased markedly as compared to LacA-control, nonexpressing cells. Results depicted in FIGS. 10A and 10B establish both that longer AD7c-NTP induced expression and longer exposure to hydrogen peroxide ($H_2O_2$) and diethyldithiocarbamic acid (DDC) lead to decreased cell viability and increased hypersensitivity, respectively.

In order to determine the reason for decreased cell viability, experiments were done to quantitatively measure apoptosis in stably transfected, CYST neuronal cells expressing AD7c-NTP; results are presented in FIG. 11. The degree of apoptosis was determined by incubating cells in the presence of $^{32}$dCTP to measure template-independent incorporation of label into fragmented DNA, a characteristic of the apoptotic mechanism of cell death. Comparison of control (uninduced, transfected cells) with 3 mM induced (indicated by B6) LacA, LacB and LacF cells clearly indicates that expression of AD7c-NTP leads to increased incorporation of $^{32}$dCTP label into cellular DNA (increased apoptosis). Variations in the incorporation of label between IPTG induced cell lines are attributed to differences in the level of AD7c-NTP expression.

The established in vitro system provides a means for screening pharmacologic agents that modulate or counteract the changes effected through AD7c-NTP expression and, ostensibly, the AD process. AD7c-NTP expression leads to up-regulation of nitric oxide synthase which, in some neuronal cells, causes oxygen free radical formation. The experiment depicted in FIG. 12 establishes that AD7c-NTP induced oxidative stress can be counteracted by pharmacologic agents. Results are expressed as the ratio of percent change in viability for experimental (AD7c-NTP induced) over control, uninduced cells. In FIG. 12, CYZ cells, stably transfected with AD7c-NTP, are induced to express AD7c-NTP and exposed to various pharmacologic agents. Hydrogen peroxide ($H_2O_2$) and diethyldithiocarbamic acid (DDC)

exacerbate cell death, while agents such pyroglutamate (PG) (and L-NAME and L-arginine) inhibit or reduce the nitric oxide synthase toxicity attributable to AD7c-NTP expression.

From the foregoing description, one skilled in the art can easily ascertain the essential characteristics of this invention, and without departing from the spirit and scope thereof, can make various changes and modifications of the invention to adapt it to various usages and conditions without undue experimentation. All patents, patent applications and publications cited herein are incorporated by reference in their entirety.

---

What is claimed is:

1. A method for the treatment of dementias of the Alzheimer's type of neuronal degeneration, said method comprising administering to an animal in need thereof an antisense oligonucleotide which is complementary to an NTP mRNA sequence corresponding to nucleotides 150–1139 of SEQ ID NO:1.

2. The method of claim 1, wherein said antisense oligonucleotide is a 15 to 40 mer.

3. The method of claim 1, wherein said antisense oligonucleotide is selected from the group consisting of SEQ ID NO:9, SEQ ID NO:10 and SEQ ID NO:11.

4. The method of claim 1, wherein said antisense oligonucleotide is deoxyribonucleic acid.

5. The method of claim 1, wherein said antisense oligonucleotide is a deoxyribonucleic acid phosphorothioate.

6. The method of claim 1, wherein said antisense oligonucleotide is a derivative of a deoxyribonucleic acid or a derivative of a deoxyribonucleic acid phosphorothioate.

7. The method of claim 1, wherein said antisense oligonucleotide is administered to said animal as part of a pharmaceutically acceptable carrier.

* * * * *

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
       (A) LENGTH: 1442 base pairs
       (B) TYPE: nucleic acid
       (C) STRANDEDNESS: double
       (D) TOPOLOGY: both (ii) MOLECULE TYPE: cDNA (ix) FEATURE:
       (A) NAME/KEY: CDS
       (B) LOCATION: 15..1139

(xi) SEQUENCE DESCRIPTION: SEQ ID NO: 1:

```
TTTTTTTTTT TGAG ATG GAG TTT TCG CTC TTG TTG CCC AGG CTG GAG TGC        50
              Met Glu Phe Ser Leu Leu Leu Pro Arg Leu Glu Cys
                1             5                  10

AAT GGC GCA ATC TCA GCT CAC CGC AAC CTC CGC CTC CCG GGT TCA AGC        98
Asn Gly Ala Ile Ser Ala His Arg Asn Leu Arg Leu Pro Gly Ser Ser
         15                  20                  25

GAT TCT CCT GCC TCA GCC TCC CCA GTA GCT GGG ATT ACA GGC ATG TGC       146
Asp Ser Pro Ala Ser Ala Ser Pro Val Ala Gly Ile Thr Gly Met Cys
     30                  35                  40

ACC CAC GCT CGG CTA ATT TTG TAT TTT TTT TTA GTA GAG ATG GAG TTT       194
Thr His Ala Arg Leu Ile Leu Tyr Phe Phe Leu Val Glu Met Glu Phe
 45                  50                  55                  60

CTC CAT GTT GGT CAG GCT GGT CTC GAA CTC CCG ACC TCA GAT GAT CCC       242
Leu His Val Gly Gln Ala Gly Leu Glu Leu Pro Thr Ser Asp Asp Pro
                 65                  70                  75

TCC GTC TCG GCC TCC CAA AGT GCT AGA TAC AGG ACT GGC CAC CAT GCC       290
Ser Val Ser Ala Ser Gln Ser Ala Arg Tyr Arg Thr Gly His His Ala
             80                  85                  90

CGG CTC TGC CTG GCT AAT TTT TGT GGT AGA AAC AGG GTT TCA CTG ATG       338
Arg Leu Cys Leu Ala Asn Phe Cys Gly Arg Asn Arg Val Ser Leu Met
         95                 100                 105

TGC CCA AGC TGG TCT CCT GAG CTC AAG CAG TCC ACC TGC CTC AGC CTC       386
Cys Pro Ser Trp Ser Pro Glu Leu Lys Gln Ser Thr Cys Leu Ser Leu
    110                 115                 120

CCA AAG TGC TGG GAT TAC AGG CGT GCA GCC GTG CCT GGC CTT TTT ATT       434
Pro Lys Cys Trp Asp Tyr Arg Arg Ala Ala Val Pro Gly Leu Phe Ile
125                 130                 135                 140

TTA TTT TTT TTA AGA CAC AGG TGT CCC ACT CTT ACC CAG GAT GAA GTG       482
Leu Phe Phe Leu Arg His Arg Cys Pro Thr Leu Thr Gln Asp Glu Val
                145                 150                 155

CAG TGG TGT GAT CAC AGC TCA CTG CAG CCT TCA ACT CCT GAG ATC AAG       530
Gln Trp Cys Asp His Ser Ser Leu Gln Pro Ser Thr Pro Glu Ile Lys
            160                 165                 170

CAT CCT CCT GCC TCA GCC TCC CAA GTA GCT GGG ACC AAA GAC ATG CAC       578
```

```
His Pro Pro Ala Ser Ala Ser Gln Val Ala Gly Thr Lys Asp Met His
        175                 180                 185

CAC TAC ACC TGG CTA ATT TTT ATT TTT ATT TTT AAT TTT TTG AGA CAG    626
His Tyr Thr Trp Leu Ile Phe Ile Phe Ile Phe Asn Phe Leu Arg Gln
        190                 195                 200

AGT CTC AAC TCT GTC ACC CAG GCT GGA GTG CAG TGG CGC AAT CTT GGC    674
Ser Leu Asn Ser Val Thr Gln Ala Gly Val Gln Trp Arg Asn Leu Gly
205                 210                 215                 220

TCA CTG CAA CCT CTG CCT CCC GGG TTC AAG TTA TTC TCC TGC CCC AGC    722
Ser Leu Gln Pro Leu Pro Pro Gly Phe Lys Leu Phe Ser Cys Pro Ser
                225                 230                 235

CTC CTG AGT AGC TGG GAC TAC AGG CGC CCA CCA CGC CTA GCT AAT TTT    770
Leu Leu Ser Ser Trp Asp Tyr Arg Arg Pro Pro Arg Leu Ala Asn Phe
                240                 245                 250

TTT GTA TTT TTA GTA GAG ATG GGG TTC ACC ATG TTC GCC AGG TTG ATC    818
Phe Val Phe Leu Val Glu Met Gly Phe Thr Met Phe Ala Arg Leu Ile
            255                 260                 265

TTG ATC TCT GGA CCT TGT GAT CTG CCT GCC TCG GCC TCC CAA AGT GCT    866
Leu Ile Ser Gly Pro Cys Asp Leu Pro Ala Ser Ala Ser Gln Ser Ala
    270                 275                 280

GGG ATT ACA GGC GTG AGC CAC CAC GCC CGG CTT ATT TTT AAT TTT TGT    914
Gly Ile Thr Gly Val Ser His His Ala Arg Leu Ile Phe Asn Phe Cys
285                 290                 295                 300

TTG TTT GAA ATG GAA TCT CAC TCT GTT ACC CAG GCT GGA GTG CAA TGG    962
Leu Phe Glu Met Glu Ser His Ser Val Thr Gln Ala Gly Val Gln Trp
                305                 310                 315

CCA AAT CTC GGC TCA CTG CAA CCT CTG CCT CCC GGG CTC AAG CGA TTC   1010
Pro Asn Leu Gly Ser Leu Gln Pro Leu Pro Pro Gly Leu Lys Arg Phe
                320                 325                 330

TCC TGT CTC AGC CTC CCA AGC AGC TGG GAT TAC GGG CAC CTG CCA CCA   1058
Ser Cys Leu Ser Leu Pro Ser Ser Trp Asp Tyr Gly His Leu Pro Pro
            335                 340                 345

CAC CCC GCT AAT TTT TGT ATT TTC ATT AGA GGC GGG GTT TCA CCA TAT   1106
His Pro Ala Asn Phe Cys Ile Phe Ile Arg Gly Gly Val Ser Pro Tyr
350                 355                 360

TTG TCA GGC TGG TCT CAA ACT CCT GAC CTC AGG TGACCCACCT GCCTCAGC   1159
Leu Ser Gly Trp Ser Gln Thr Pro Asp Leu Arg
365                 370                 375

TCCAAAGTGC TGGGATTACA GGCGTGAGCC ACCTCACCCA GCCGGCTAAT TTAGATAA   1219

AAATATGTAG CAATGGGGGG TCTTGCTATG TTGCCCAGGC TGGTCTCAAA CTTCTGGCC   1279

CATGCAATCC TTCCAAATGA GCCACAACAC CCAGCCAGTC ACATTTTTTA AACAGTTA   1339

TCTTTATTTT AGTATACTAG AAAGTAATAC AATAAACATG TCAAACCTGC AAATTCAG   1399

GTAACAGAGT TCTTTTATAA CTTTTAAACA AAGCTTTAGA GCA                   1442

(2) INFORMATION FOR SEQ ID NO: 2:

(i) SEQUENCE CHARACTERISTICS:
        (A) LENGTH: 375 amino acids
        (B) TYPE: amino acid
        (D) TOPOLOGY: linear (ii) MOLECULE TYPE: protein (xi) SEQUENCE DESCRIPTION: SEQ ID NO: 2:

Met Glu Phe Ser Leu Leu Leu Pro Arg Leu Glu Cys Asn Gly Ala Ile
 1               5                  10                  15

Ser Ala His Arg Asn Leu Arg Leu Pro Gly Ser Ser Asp Ser Pro Ala
            20                  25                  30
```

```
Ser Ala Ser Pro Val Ala Gly Ile Thr Gly Met Cys Thr His Ala Arg
        35                  40                  45

Leu Ile Leu Tyr Phe Phe Leu Val Glu Met Glu Phe Leu His Val Gly
        50                  55                  60

Gln Ala Gly Leu Glu Leu Pro Thr Ser Asp Asp Pro Ser Val Ser Ala
65                  70                  75                  80

Ser Gln Ser Ala Arg Tyr Arg Thr Gly His His Ala Arg Leu Cys Leu
                85                  90                  95

Ala Asn Phe Cys Gly Arg Asn Arg Val Ser Leu Met Cys Pro Ser Trp
                100                 105                 110

Ser Pro Glu Leu Lys Gln Ser Thr Cys Leu Ser Leu Pro Lys Cys Trp
            115                 120                 125

Asp Tyr Arg Arg Ala Ala Val Pro Gly Leu Phe Ile Leu Phe Phe Leu
        130                 135                 140

Arg His Arg Cys Pro Thr Leu Thr Gln Asp Glu Val Gln Trp Cys Asp
145                 150                 155                 160

His Ser Ser Leu Gln Pro Ser Thr Pro Glu Ile Lys His Pro Pro Ala
                165                 170                 175

Ser Ala Ser Gln Val Ala Gly Thr Lys Asp Met His His Tyr Thr Trp
                180                 185                 190

Leu Ile Phe Ile Phe Ile Phe Asn Phe Leu Arg Gln Ser Leu Asn Ser
            195                 200                 205

Val Thr Gln Ala Gly Val Gln Trp Arg Asn Leu Gly Ser Leu Gln Pro
        210                 215                 220

Leu Pro Pro Gly Phe Lys Leu Phe Ser Cys Pro Ser Leu Leu Ser Ser
225                 230                 235                 240

Trp Asp Tyr Arg Arg Pro Pro Arg Leu Ala Asn Phe Val Phe Leu
                245                 250                 255

Val Glu Met Gly Phe Thr Met Phe Ala Arg Leu Ile Leu Ile Ser Gly
            260                 265                 270

Pro Cys Asp Leu Pro Ala Ser Ala Ser Gln Ser Ala Gly Ile Thr Gly
        275                 280                 285

Val Ser His His Ala Arg Leu Ile Phe Asn Phe Cys Leu Phe Glu Met
290                 295                 300

Glu Ser His Ser Val Thr Gln Ala Gly Val Gln Trp Pro Asn Leu Gly
305                 310                 315                 320

Ser Leu Gln Pro Leu Pro Pro Gly Leu Lys Arg Phe Ser Cys Leu Ser
                325                 330                 335

Leu Pro Ser Ser Trp Asp Tyr Gly His Leu Pro Pro His Pro Ala Asn
                340                 345                 350

Phe Cys Ile Phe Ile Arg Gly Gly Val Ser Pro Tyr Leu Ser Gly Trp
            355                 360                 365

Ser Gln Thr Pro Asp Leu Arg
370                 375

(2) INFORMATION FOR SEQ ID NO: 3:

(i) SEQUENCE CHARACTERISTICS:
        (A) LENGTH: 1381 base pairs
        (B) TYPE: nucleic acid
        (C) STRANDEDNESS: double
        (D) TOPOLOGY: both (ii) MOLECULE TYPE: cDNA (xi) SEQUENCE DESCRIPTION: SEQ ID NO: 3:
```

-continued

| | |
|---|---|
| TTTTTTTTTT GAGATGGAGT TTTCGCTCTT GTTGCCCAGG CTGGAGTGCA ATGGCGCAAT | 60 |
| CTCAGCTCAC CGCAACCTCC GCCTCCCGGG TTCAAGCGAT TCTCCTGCCT CAGCCTCCC | 120 |
| AGTAGCTGGG ATTACAGGCA TGTGCACCAC GCTCGGCTAA TTTTGTATTT TTTTTTAGT | 180 |
| GAGATGGAGT TTAACTCCAT GTTGGTCAGG CTGGTCTCGA ACTCCCGACC TCAGATGAT | 240 |
| TCCCGTCTCG GCCTGCCCAA AGTGCTGAGA TTACAGGCAT GAGCCACCAT GCCCGGCCT | 300 |
| TGCCTGGCTA ATTTTTGTGG TAGAAACAGG GTTTCACTGA TGTTGCCCAA GCTGGTCTC | 360 |
| TGAGCTCAAG CAGTCCACCT GCCTCAGCCT CCCAAAGTGC TGGGATTACA GGCGTCAGC | 420 |
| GTGCCTGGCC TTTTTATTTT ATTTTTTTTA AGACACAGGT GTACCACTCT TACCCAGGA | 480 |
| GAAGTGCAGT GGTGTGATCA CAGCTCACTG CAGCCTTCAA CTCCTGAGAT CAAGCAATC | 540 |
| TCCTGCCTCA GCCTCCCAAG TAGCTGGGAC CAAAGACATG CACCACTACA CCTGGTAAT | 600 |
| TTTATTTTTA TTTTTAATTT TTTGAGACAG AGTCTCACTC TGTCACCCAG GCTGGAGTG | 660 |
| AGTGGCGCAA TCTTGGCTCA CTGCAACCTC TGCCTCCCGG GTTCAAGTTA TTCTCCTGC | 720 |
| CCAGCCTCCT GAGTAGCTGG GACTACAGGC GCCCACCACG CCTAGCTAAT TTTTTTGTA | 780 |
| TTTTAGTAGA GATGGGGTTT CACCATGTTC GCCAGGTTGA TCTTGATCTC TTGACCTTG | 840 |
| GATCTGCCTG CCTCGGCCTA CCCAAAGTGC TGGGATTACA GGTCGTGACT CCACGCCGG | 900 |
| CTATTTTAA TTTTTGTTTG TTTGAAATGG AATCTCACTC TGTTACCCAG GTCGGAGTG | 960 |
| AATGGCAAAT CTCGGCTACT CGCAACCTCT GCCTCCCGGG TCAAGCGATT CTCCTGTC | 1020 |
| AGCCTCCCAA GCAGCTGGGA TTACGGGACC TGCACCACAC CCCGCTAATT TTTGTATT | 1080 |
| CATTAGAGGC GGGTTTACCA TATTTGTCAG GCTGGGTCTC AAACTCCTGA CCTCAGGT | 1140 |
| CCCACCTGCC TCAGCCTTCC AAAGTGCTGG GATTACAGGC GTGAGCCACC TCACCCAG | 1200 |
| GGCTAATTTG GAATAAAAAA TATGTAGCAA TGGGGGTCTG CTATGTTGCC CAGGCTGG | 1260 |
| TCAAACTTCT GGCTTCAGTC AATCCTTCCA AATGAGCCAC AACACCCAGC CAGTCACA | 1320 |
| TTTTAAACAG TTACATCTTT ATTTTAGTAT ACTAGAAAGT AATACAATAA ACATGTCA | 1380 |
| C | 1381 |

(2) INFORMATION FOR SEQ ID NO: 4:

(i) SEQUENCE CHARACTERISTICS:
        (A) LENGTH: 1418 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 4:

| | |
|---|---|
| TTTTTTTTTT GAGATGGAGT TTCGCTCTT GTTGCCCAGG CTGGAGTGCA ATGGCGCAAT | 60 |
| CTCAGCTCAC CGCAACCTCC GCCTCCCGGG TTCAAGCGAT TCTCCTGCCT CAGCCTCCC | 120 |
| AGTAGGCTGG GATTACAGGC ATGTGCACCA CGCTCGGCTA ATTTTGTATT TTTTTTTAG | 180 |
| AGAGATGGAG TTTCTCCATG TTGGTCAGGC TGGTCTCGAA CTCCGACCTC AGATGATCC | 240 |
| CCCGTCTCGG CCTCCCAAAG TGCTAGATAC AGGACTGAGC ACCATGCCCG GCCTCTGCC | 300 |
| GGCTAATTTT TGTGGTAGAA ACAGGGTTTC ACTGATGTGC CAAGCTGGT CTCCTGAGC | 360 |
| CAAGCAGTCC ACCTGCCTCA GCCTCCCAAA GTGCTGGGAT TACAGGCGTG CAGCCGTGC | 420 |
| TGGCCTTTTT ATTTTATTTT TTTTAAGACA CAGGTGTCCC ACTCTTACCC AGGATGAAG | 480 |
| GCAGTGGTGT GATCACAGCT CACTGCAGCC TTCAACTCTG AGATCAAGCA TCCTCCTGC | 540 |

-continued

```
TCAGCCTCCC AAAGTAGCTG GGACCAAAGA CATGCACCAC TACACCTGGC TAATTTTTA      600

TTTTATTTTT AATTTTTTGA GACAGAGTCT CAACTCTGTC ACCCAGGCTG GAGTGCAGT      660

GCGCAATCTT GGCTCACTGC AACCTCTGCC TCCCGGGTTC AAGTTATTCT CCTGCCCCA      720

CCTCCTGAGT AGCTGGGACT ACAGGCGCCC ACCACGCCTA GCTAATTTTT TTGTATTTT      780

AGTAGAGATG GGGTTTCACC ATGTTCGCCA GGTTGATGCT AGATCTCTTG ACCTTGTGA      840

CTGCCTGCCT CGGCCTCCCA AAGTGCTGGG ATTACAGGAC GTGACGCCCA CCGCCCGGC      900

TATTTTTAAT TTTTGTTTGT TTGAAATGGA ATCTCACTCT GTTACCCAGG CTGGAGTGC      960

ATGGCCAAAT CTCGGCTCAC TGCAACCTCT GCCTCCCGGG CTCAAGCGAT TCTCCTGT      1020

CAGCCTCCCA AGCAGCTGGG ATTACGGGCA CCTGCACCAC ACCCCGCTAA TTTTTGTA      1080

TTCATTAGAG GCGGGGTTTC ACCATATTTG TCAGGCTGGT CTCAAACTCC TGACCTCA      1140

TGACCCACCT GCCTCAGCCT TCCAAAGTGC TGGGATTACA GGCGTGACGC CTCACCCA      1200

CGGCTAATTT AGATAAAAAA ATATGTAGCA ATGGGGGGTC TTGCTATGTT GCCCAGGC      1260

GTCTCAAACT TCTGGCTTCA TGCAATCCTT CCAAATGAGC CACAACACCC AGCCAGTC      1320

ATTTTTAAAC AGTTACATCT TTATTTTAGT ATACTAGAAA GTGATACGAT AACATGGC      1380

AACCTGCAAA TTCGAGTAGT ACAGAGTCTT TTATAACT                            1418
```

(2) INFORMATION FOR SEQ ID NO: 5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

```
TGTCCCACTC TTACCCAGGA TG                                              22
```

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

```
AAGCAGGCAG ATCACAAGGT CCAG                                            24
```

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

```
AATGGATGAC GATATCGCTG                                                 20
```

(2) INFORMATION FOR SEQ ID NO: 8:

(i) SEQUENCE CHARACTERISTICS:

```
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

ATGAGGTAGT CTGTCAGGT                                                    19

(2) INFORMATION FOR SEQ ID NO: 9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

TTCATCCTGG GTAAGAGTGG GACACCTGTG                                        30

(2) INFORMATION FOR SEQ ID NO: 10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

TGGTGCATGT CTTTGGTCCC AGCTAC                                            26

(2) INFORMATION FOR SEQ ID NO: 11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

ATCAACCTGG CGAACATGGT GAACCCCATC                                        30

(2) INFORMATION FOR SEQ ID NO: 12:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

CACTGCACTT NCCA                                                         14

(2) INFORMATION FOR SEQ ID NO: 13:

(i) SEQUENCE CHARACTERISTICS:
        (A) LENGTH: 14 base pairs
        (B) TYPE: nucleic acid
        (C) STRANDEDNESS: single
        (D) TOPOLOGY: linear
```

-continued (ii) MOLECULE TYPE: cDNA (xi) SEQUENCE DESCRIPTION: SEQ ID NO: 13:

CCAGGTGTAG NCCA 14

(2) INFORMATION FOR SEQ ID NO: 14:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

CAAGGTCCAG NCCA 14